(12) United States Patent
Berzak et al.

(10) Patent No.: US 7,942,870 B2
(45) Date of Patent: May 17, 2011

(54) APPARATUS AND METHOD FOR ACCURATELY DELIMITED CRYOABLATION

(75) Inventors: Nir Berzak, Zikhron-Yaakov (IL); Roni Zvuloni, Haifa (IL); Uri Amir, Or Yehuda (IL)

(73) Assignee: Galil Medical Ltd., Yokneam (IL)

( * ) Notice: Subject to any disclaimer, the term of this patent is extended or adjusted under 35 U.S.C. 154(b) by 1031 days.

(21) Appl. No.: 11/240,556

(22) Filed: Oct. 3, 2005

(65) Prior Publication Data

US 2006/0079867 A1 Apr. 13, 2006

Related U.S. Application Data

(63) Continuation-in-part of application No. PCT/IL2004/000303, filed on Apr. 1, 2004.

(60) Provisional application No. 60/459,608, filed on Apr. 3, 2003.

(51) Int. Cl.
*A61B 18/02* (2006.01)

(52) U.S. Cl. .............. 606/21; 606/23; 606/20

(58) Field of Classification Search .......... 606/20–26; 128/898
See application file for complete search history.

(56) References Cited

U.S. PATENT DOCUMENTS

| | | | |
|---|---|---|---|
| 5,647,868 A * | 7/1997 | Chinn | 606/21 |
| 5,800,487 A | 9/1998 | Mikus et al. | |
| 5,899,897 A * | 5/1999 | Rabin et al. | 606/21 |
| 6,074,412 A | 6/2000 | Mikus et al. | |
| 6,139,544 A * | 10/2000 | Mikus et al. | 606/21 |
| 6,142,991 A | 11/2000 | Schatzberger | |
| 6,505,629 B1 | 1/2003 | Mikus et al. | |
| 7,081,111 B2 * | 7/2006 | Svaasand et al. | 606/21 |
| 2002/0049436 A1 | 4/2002 | Zvuloni et al. | |
| 2002/0198518 A1 | 12/2002 | Mikus et al. | |
| 2003/0060762 A1 | 3/2003 | Zvuloni et al. | |

FOREIGN PATENT DOCUMENTS

| | | |
|---|---|---|
| EP | 0395307 | 10/1990 |
| EP | 0947172 | 10/1999 |
| JP | 02-299647 | 12/1990 |
| JP | 11-332872 | 12/1999 |
| JP | 2000-516696 | 12/2000 |
| WO | WO 80/00789 | 1/1980 |
| WO | 83/03961 A1 | 11/1983 |
| WO | WO 98/04221 | 2/1998 |

(Continued)

OTHER PUBLICATIONS

Hartgerink et al. "Self-Assembling Peptide Nanotubes", Journal of the American Chemical Society, 118: 43-50, 1996.

(Continued)

*Primary Examiner* — Michael Peffley
*Assistant Examiner* — Ronald Hupczey, Jr.
(74) *Attorney, Agent, or Firm* — Fredrikson & Byron, P.A.

(57) ABSTRACT

The present invention is of a system and method for accurate cryoablation, useable to enhance a surgeon's ability to accurately cryoablate a selected cryoablation target and to limit cryoablation to that selected target. Presented are apparatus and method for accurately delimiting a cryoablation volume, for minimizing damage to tissues surrounding a cryoablation volume, and for real-time visualization of a border of a cryoablation volume during cryoablation. Also presented are a method for mildly heating tissues during cryoablation, cryoprobes operable to simultaneously cool first tissues while heating second tissues, and cryoprobes operable to cool tissues extending in a first lateral direction from those probes while not substantially cooling tissues extending in a second lateral direction from those probes.

25 Claims, 21 Drawing Sheets

FOREIGN PATENT DOCUMENTS

| WO | WO 99/58652 | 11/1999 |
|---|---|---|
| WO | WO 01/10457 | 2/2001 |
| WO | WO 03/059247 A2 * | 7/2003 |
| WO | WO 2004/052773 | 6/2004 |
| WO | WO 2004/060791 | 7/2004 |
| WO | WO 2005/031362 | 7/2005 |

OTHER PUBLICATIONS

Ajayan et al. "Applications of Carbon Nanotubes", Topics of Applied Physics, 80: 391-425, 2001.

Görbitz "Nanotube Formation by Hydrophobic Dipeptides", Chemistry, 7(23): 5153-5159, 2001.

Reches et al. "Amyloid Fibril Formation by Pentapeptide and Tetrapeptide Fragments of Human Calcitonin", Journal of Biological Chemistry, 277(38): 35475-35480, 2002.

Haldar et al. "First Crystallographic Signature of the Highly Ordered Supramolecular Helical Assemblage From a Tripeptide Containing a Non-Coded Amino Acid", Tetrahedron Letters, 43(14): 2653-2656, 2002.

Maji et al. "Fibril-Forming Model Synthetic Peptides Containing 3-Aminophenylacetic Acid", Tetrahedron, 58(43): 8695-8702, 2002.

Hartgerink et al. "Peptide Nanotubes and Beyond", Chemistry, A European Journal, 4(8): 1367-1372, 1998.

Ghadiri et al. "Self-Assembling Organic Nanotubes Based on a Cyclic Peptide Architecture", Nature, 366: 324-327, 1993.

Horne et al. "A Heterocyclic Peptide Nanotube", Journal of the American Chemical Society, 125(31): 9372-9376, 2003.

Reches et al. "Casting Metal Nanowires Within Discrete Self-Assembled Peptide Nanotubes", Science, 300(5619): 625-627, 2003.

Adekore et al. "Carbon Nanotubes", p. 1-11, 2001.

Brauer "GB-245 Nanotubes: Directions and Techno", BCC, p. 1-14, 2000.

Martin et al. "The Emerging Field of Nanotube Biotechnology", Nature Reviews, 2: 29-37, 2003.

Zhang et al. "Design of Nanostructured Biological Materials Through Self-Assembly of Peptides and Proteins", Current Opinion in Chemical Biology, 6: 865-871, 2002.

Daenen et al. "The Wondrous World of Carbon Nanotubes", p. 1-8, 2003.

Grady et al. "Axe-Txe, A Broad-Spectrum Proteic Toxin-Antitoxin System Specified by a Multidrug-Resistant, Clinical Isolate of Enterococcus Faecium", Molecular Biology, 47(5): 1419-1432, 2003. Abstract, p. 1424, col. 1-p. 1426, col. 2, Fig.5.

Cherny et al. "The YefM Antitoxin Defines a Family of Natively Unfolded Proteins", The Journal of Biological Chemistry, 279(9): 8252-8261, 2004.

Engelberg-Kulka et al. "Bacterial Programmed Cell Death Systems as Targets for Antibiotics", Trends in Microbiology, 12(2): 66-71, 2004.

Forloni et al. "Anti-Amyloidogenic Activity of Tetracyclines: Studies In Vitro", FEBS Letters, 487(3): 404-407, 2001. Abstract, Results, Figs.1, 3.

Lansbury Jr. "Following Nature's Anti-Amyloid Strategy", Nature Biotechnology, 19(2): 112-113, 2001.

Grateau "Le Curli du Coli: Une Variété Physiologique d'Amylose", Medecine Sciences, 18(6-7): 664, 2002.

Cherny et al. "The Formation of *Escherichia coli* Curli Amyloid Fibrils Is Mediated by Prion-Like Peptide Repeats", Journal of Molecular Biology, 352(2): 245-252, 2005.

Examiner's Report Dated Aug. 8, 2008 From the Government of Australia, IP Australia Re.: Application No. 2005218066.

Haldar et al. "First Crystallographic Signature of the Highly Ordered Supramolecular Helical Assemblage From a Tripeptide Containing a Non-Coded Amino Acid", Tetrahedron Letters, 43(14): 2653-2656, 2002. Abstract.

Translation of Notice of Reason for Rejection Dated Aug. 14, 2009 From the Japanese Patent Office Re.: Application No. 2006-507599.

Translation of Notice of Reason for Rejection Dated Feb. 26, 2010 From the Japanese Patent Office Re.: Application No. 2006-507599.

EP 04725137 European Supplemental Search Report dated Sep. 14, 2010.

* cited by examiner

APPARATUS AND METHOD FOR ACCURATELY DELIMITED CRYOABLATION

RELATED APPLICATIONS

This application is a Continuation In Part of PCT Application No. PCT/IL2004/000303, filed on Apr. 1, 2004, which claims the benefit of U.S. Provisional Patent Application No. 60/459,608, filed Apr. 3, 2003, which applications are hereby incorporated by reference.

FIELD AND BACKGROUND OF THE INVENTION

The present invention relates to an apparatus and method for accurately delimited cryoablation of unwanted body tissues. More particularly, the present invention relates to method and apparatus for cryoablating a selected target volume of body tissue while surrounding or partially surrounding said target volume with a protective envelope of mildly heated tissue, so as to enhance accuracy of delimitation of the volume of cryogenic destruction, and so as to minimize the volume of tissue, exterior to the selected target volume, damaged by cryogenic cooling.

In recent years, cryoablation of tissues has become an increasingly popular method of treatment for a variety of pathological conditions. Malignancies in body organs such as the breast, prostate, kidney, liver, and other organs are successfully treated by cryoablation, and a variety of non-malignant pathological conditions, such as benign prostate hyperplasia, benign breast tumors, and similar growths are also well treated by cryoablation of unwanted tissues. Certain cases of intractable chronic pain are also treatable through cryosurgery, by cryoablation of selected nervous tissue.

Cryoablation of pathological tissues or other unwanted tissues is typically accomplished by utilizing imaging modalities, such as x-ray, ultrasound, CT, and MRI, to identify a locus for ablative treatment, then inserting one or more cryoprobes into that selected treatment locus, then cooling the treatment heads of the inserted cryoprobes sufficiently to cause the tissues surrounding the treatment heads to reach cryoablation temperatures, typically below about −40° C.

Tissues thus cooled are thereby caused to loose their functional and structural integrity. Cancerous cells cease growing and multiplying, and cryoablated tumor tissue materials, whether from malignant tumors or from benign growths, lose their structural integrity and are subsequently sloughed off or absorbed by the body.

The principle danger and disadvantage of cryosurgical ablative treatment, however, is the danger of partially or completely destroying the functional and structural integrity of healthy tissues near the treatment locus, thereby impeding the patient's recovery from the surgical procedure and potentially causing serious and long-term deleterious effects on the patient's health and on his quality of life.

In particular, two well-known limitations inherent in currently known cryoablation technique are primarily responsible for damage caused to healthy tissue while cryoablating pathological tissue.

Using terms defined hereinbelow, we would say that the first problem is that in all cryoablation the "ablation volume", a first volume within which tissue structure and functionality are destroyed, is inevitably surrounded by a "damage envelope", a second volume within which tissue structure and function are damaged. Tissues in the damage envelope are exposed to temperatures which, although not sufficiently cold to thoroughly cryoablate those tissues and wholly destroy their physiological functionality, yet are cold enough to do significant damage to those tissues, impair their functionality, and significantly alter cellular and other structures therein. To reliably ablate a first selected target volume of tissue, one is inevitably obliged to damage second volume of tissue surrounding that first selected volume.

The second problem is that cryosurgery is difficult to control, because the border between the ablation volume and the damage envelope is not directly visible under any known imaging modalities. Although the borders of the ice-ball which forms around the cold operating tip of a functioning cryoprobe is visible under ultrasound or MRI imaging modalities, the border of the ablation volume, the volume within which cell functionality is reliably destroyed, is itself not directly visible under known imaging modalities, and it's position, somewhere within the visible ice-ball, must be estimated or indirectly detected or guessed.

Various devices and methods have been proposed to enable cryoablation of pathological tissue while limiting damage to non-pathological tissue. These fall roughly into two categories: devices and methods which protect tissues by preventing excessive cooling of those tissues during a cryoablation procedure in their vicinity, and devices and methods which enable accurate placement of cryoprobes used in cryoablation, so as to successfully concentrate the cooling effect of such cryoprobes at or near pathological tissue, thereby minimizing unwanted cooling of non-pathological tissue.

An example of the former category is the well-known technique of introducing a heating device or a heated fluid into the urethra of a patient, thereby heating the urethra and tissues adjacent to it during cryoablation of portions of the prostate, thereby helping to protect the urethra from damage while prostate tissues nearby are being cooled to cryoablation temperatures. U.S. Pat. No. 6,505,629 to Mikus et. al. teaches a similar method, using a heating probe to protect an object, the neuro-vascular bundle, during cryoablation of the prostate, by interposing a heating probe between that object and a cooling cryoprobe.

An example of the latter category is provided by U.S. Pat. No. 6,142,991 to Schatzberger. Schatzberger describes a high resolution cryosurgical method and device for treating a patient's prostate, including the steps of (a) introducing a plurality of cryosurgical probes to the prostate, the probes having a substantially small diameter, the probes being distributed across the prostate, so as to form an outer arrangement of probes adjacent the periphery of the prostate and an inner arrangement of probes adjacent the prostatic urethra; and (b) producing an ice-ball at the end of each of the cryosurgical probes, so as to locally freeze a tissue segment of the prostate. Schatzberger's apparatus includes (a) a plurality of cryosurgical probes of small diameter, the probes being for insertion into the patient's organ, the probes being for producing ice-balls for locally freezing selected portions of the organ; (b) a guiding element including a net of apertures for inserting the cryosurgical probes therethrough; and (c) an imaging device for providing a set of images, the images being for providing information on specific planes located at specific depths within the organ, each of the images including a net of marks being correlated to the net of apertures of the guiding element, wherein the marks represent the locations of ice-balls which may be formed by the cryosurgical probes when introduced through the apertures of the guiding element to the distinct depths within the organ.

Thus, Schatzberger's method and apparatus enable a surgeon to place a set of cryoablation probes within a prostate with relatively high accuracy, and to operate those probes to ablate selected tissues while avoiding, to a large extent, inadvertent and undesirable ablation of healthy tissues near the ablation site. Schatzberger also demonstrates that by utilizing multiple small cryoprobes in a dense array, the volume of the damage envelope may to some extent be reduced.

However, neither Schatzberger's technique nor any other known technique has proven sufficiently accurate to prevent damage to peripheral tissues in general. An ablation target ablated according to the methods of Schatzberger is still surrounded by broad envelope of damaged tissue. Further, Mikus' invention, while solving the specific problem of unwanted damage to a specific object, does not address the general problem of the overall "sloppiness" of the cryoablation procedure. Cryoablation, as practiced under all known prior art methods, results in cryoablation of a first volume, only approximately conforming to an intended cryoablation target, which first volume is surrounded by a second volume of healthy tissue, unavoidably damaged.

Thus there is a widely recognized need for, and it would be highly advantageous to have, apparatus and method for cryoablation which results in reduced volume of damaged tissue surrounding the selected cryoablation target, yet enables full and reliable cryoablation of the selected target.

As mentioned above, a second basic problem in cryosurgery technology relates to the difficulty experienced by surgeons in knowing the exact extent of the tissue which will be ablated by a given cryoablation procedure. The ice-ball produced by a functioning cryoprobe is visible under ultrasound and other imaging modalities, but the delimitation of the cryoablation volume (the area of total cell destruction) within that iceball is not directly visible under known imaging technologies. The surgeon, who in the case of treatment of a malignancy must err on the side of caution, often ablates more tissue than was really necessary, and damages more additional tissue than was really necessary, because he is unable to accurately command the exact delimitation of the destruction volume he creates, and is further unable to accurately observe, in real time, the actual border of the destruction volume created by his cryoablative intervention.

Thus there is a widely recognized need for, and it would be highly advantageous to have, a cryosurgery apparatus and method enabling accurate delimitation of an ablation volume.

With respect to prior art relevant to another aspect of the invention, Mikus op. cit. teaches use of low-pressure helium supplied to a cryoprobe having a Joule-Thomson orifice, to supply heating to a probe. According to Mikus, low-pressure helium is used in place of high-pressure helium, to assure that a tissues will not be heated beyond a temperature which would be destructive to those heated tissues.

Use of low-pressure helium for heating a Joule-Thomson probe does indeed ensure that a desired maximum temperature of the probe will not be exceeded. There is, however, a disadvantage to use of low-pressure helium for heating such a probe, namely that the heating capacity of a probe so heated is somewhat limited. Use of low pressure of the supplied helium, supplied through a small-diameter gas-supply conduit, insures that only a relatively small quantity of helium gas will be passed through the Joule-Thomson orifice per unit of time. This limitation is particularly noticeable when the method is applied to probes of small dimensions. Yet, as taught by Schatzberger op. cit., small-diameter cryosurgical devices are desirable in many cryosurgery contexts, and small diameter cryoprobes comprise even smaller diameter gas input supply conduits. Thus, use of low-pressure helium to heat today's miniaturized cryoprobes substantially limits the heating ability of such a probe.

Thus, there is a widely recognized need for, and it would be highly desirable to have, a device and method for Joule-Thomson heating of a probe, which device and method provide heating to an upper limit of temperature, thereby protecting heated tissues from overheating, provide for a high throughput of gas, and therefore provide a higher heating capacity than that provided by a Joule-Thomson probe heated by expansion of low-pressure helium gas.

Note is here taken of three additional prior art documents presenting devices or methods having elements in common with devices and methods presented herein, or presenting devices for which new uses are presented hereinbelow.

First, Zvuloni et. al. in U.S. patent application Ser. No. 10/255,834 (Publication No. 2003-0060762-A1) teaches use, in a cooling cryoprobe, of a gas mixture comprising both a cryogenic cooling gas and a heating gas such as helium. Zvuloni contemplates use of such a gas so as to enable fine control of cooling, and to enable leak detection in a balloon catheter based on detection of trace amounts of helium.

Second, in PCT application IL02/01062 Zvuloni et. al. teach use of a cryoprobe having a cooling tip and a heated shaft, operable to protect tissues adjacent to the shaft of such a probe, which shaft, absent a heating or insulating effect in the shaft, would in some circumstances be sufficiently cooled by passage therein of exhaust cooling gasses from the probes's cooling tip to risk damaging, by cooling, healthy tissues adjacent to that shaft.

Third, in U.S. Pat. No. 6,074,412, Mikus et. al. teach a probe having both heating elements and cooling elements, yet the heating and cooling elements of Mikus' probe are designed for, and can only be used, sequentially and not simultaneously.

SUMMARY OF THE INVENTION

The present invention is of a system and method for accurate cryoablation allowing enhancing a surgeon's ability to accurately cryoablate a selected cryoablation target and to limit cryoablation to that selected target. The present invention encompasses (a) an apparatus and method for accurately delimiting a cryoablation volume; (b) an apparatus and method for minimizing damage to tissues surrounding a cryoablation volume; (c) an apparatus and method for real-time visualization of a border of a cryoablation volume during cryoablation; (d) an apparatus and method for mildly heating tissues during cryoablation; (e) a cryoprobe operable to simultaneously cool first tissues while heating second tissues; and (f) a method for accurate cryoablation of a selected target.

According to one aspect of the present invention there is provided a method for sharply delimiting a cryoablation volume when cryoablating a selected cryoablation target in the body of a patient, comprising defining a three-dimensional shape as a border of a cryoablation target; inserting into the patient a plurality of probes each comprising at least one treatment module; positioning the probes so that a first set of the treatment modules is adjacent to the defined shaped border and interior to the selected cryoablation target, and a second set of the treatment modules is adjacent to the defined shaped border and exterior to the selected cryoablation target; cooling the first set of treatment modules to cryoablation temperatures, thereby cryoablating tissues within the cryoablation target and adjacent to the border; and heating the second set of treatment modules during the cooling of the first set of treatment modules, thereby creating a sharp temperature gradient at a vicinity of the shaped border of the cryoablation target, thereby sharply delimiting the cryoablation volume.

According to further features in preferred embodiments of the invention described below, at least one of the plurality of probes comprises at least two independently controllable treatment modules.

According to still further features in the described preferred embodiments, the method further comprises heating a first of the independently controllable treatment modules while cooling a second of the independently controllable treatment modules, preferably heating the first independently controllable treatment module by expansion, through a Joule-Thomson orifice, of a mixture of cooling gas and heating gas.

According to still further features in the described preferred embodiments the method further comprises orienting the probes with respect to the cryoablation target by positioning, exterior to a patient and in a position having a known spatial relationship to the cryoablation target, a template having an array of apertures each operable to orient a probe passing therethrough to a predetermined angle with respect to the template; and passing a plurality of the probes through ones of the array of apertures, and thence into the patient, thereby orienting the inserted probes with respect to the cryoablation target. The template may be positioned at a perineum of a patient. Preferably the template is designed and constructed to ensure parallel orientations of a plurality of cryoprobes inserted therethrough. Preferably at least one of the probes comprises an external marking on the probe, designed and constructed to render visible to an operator a depth of penetration of the probe through the template. Preferably, the second set of treatment modules surrounds the cryoablation target.

According to another aspect of the present invention there is provided a method for minimizing damage to tissues surrounding a cryoablation target when cryoablating the target, comprising defining a three-dimensional shape as a border of a cryoablation target; inserting into a patient a plurality of probes each comprising at least one treatment module; positioning the probes so that a first set of the treatment modules is inside the cryoablation target, and a second set of the treatment modules is exterior to the target and surrounds at least a portion of the target; cooling the first set of treatment modules to cryoablation temperatures, thereby ablating tissues within the target; and heating the second set of treatment modules during cooling of the first set of treatment modules, thereby preventing cooling of tissues surrounding the cryoablation target, thereby minimizing damage to tissues surrounding the cryoablation target while cryoablating the target.

According to further features in preferred embodiments of the invention the second set of treatment modules entirely surrounds the cryoablation target. Cooling of the first set of treatment modules may entirely ablate an organ, such as a prostate, or may entirely ablate a tumor.

Preferably, each treatment module of the first set of treatment modules is positioned adjacent to at least one treatment module of the second set of treatment modules.

According to yet another aspect of the present invention there is provided an apparatus for accurate delimitating a cryoablation volume, comprising: a positioning device for positioning a plurality of cryoprobes within and around a cryoablation target, at least one probe operable to heat tissues adjacent to a border of the cryoablation target and external to the target, while cooling tissues adjacent to the border of the cryoablation target and internal to the target.

Preferably, the at least one probe comprises a plurality of independently controllable and simultaneously operable treatment modules, each of the modules being operable to cool adjacent tissues and also being operable to heat adjacent tissues. The independently controllable treatment modules may be coolable by Joule-Thomson cooling, and/or heatable by Joule-Thomson heating. The probe may comprise two treatment modules laterally positioned, such that the probe is operable to cool along a first face of a longitudinally extended section thereof, while heating along a second face of the longitudinally extended section thereof. Alternatively, the probe may comprise two treatment modules longitudinally positioned, such that the probe is operable to cool a distal treatment module while heating a proximal treatment module, and is further operable to cool the proximal treatment module while heating the distal treatment module.

The positioning device may comprise a template presenting an array of apertures for inserting the probes therethrough, the apertures being operable to guide placement of the probes within and around a cryoablation target. The apparatus may further comprise a plurality of probes, each operable to pass through one of the apertures prior to insertion into a body of a patient, and may further comprise a probe having external markings designed and constructed to render visible to an operator a degree of penetration of the probe through one of the apertures.

Preferably, the apparatus comprises a gas supply system operable to individually control a supply of gas to each of the probes.

Preferably, at least one of the probes comprises a plurality of treatment modules.

The gas supply system may be operable to supply gas to a cryoprobe which comprises a plurality of treatment modules, and further operable to individually control supply of gas to each module of the plurality of treatment modules.

The apparatus may be operable to supply a mixture of cooling gas and heating gas to one of the probes, or to supply a mixture of cooling gas and heating gas to one of the treatment modules. Preferably the apparatus is further operable to supply a selected mixture of cooling gas and heating gas, under control of a control module.

According to still another aspect of the present invention there is provided a method for real-time visualization of a border of a cryoablation volume during cryoablation of a cryoablation target, comprising creating a cryoablation volume having a well-defined delimitation surface, by inserting into a cryoablation target a plurality of probes each having a treatment module operable to cool tissues to cryoablation temperatures; inserting into a patient around the cryoablation target a plurality of probes each having a treatment module operable to heat tissues; and heating those of the treatment modules positioned outside the target while cooling to cryoablation temperatures those of the treatment modules positioned inside the target, thereby creating a cryoablation volume having a delimited surface extending between the plurality of heated modules and the plurality of cooled modules, and thereby having a known positional relationship to the treatment modules of the probes; and utilizing visualization modalities to display to an operator positions of at least some of the cooling and heating treatment modules, thereby enabling an operator, seeing a display of the positions of the cooling and heating modules, to accurately infer a position of the delimited cryoablation border.

The method may further comprise displaying a border of a cryoablation target. The target border may be visualized utilizing equipment selected from a group including ultrasound equipment, MRI equipment, x-ray equipment, and fluoroscope equipment. The target border may be rendered visible by digital display of a mathematical model of the target. Preferably, at least some probes of the plurality of probes comprise a marker, visible under an imaging modality, marking a border between first treatment modules of the probes and second treatment modules of the probes.

According to an additional aspect of the present invention there is provided an apparatus for adjustable heating of body tissues, comprising: a probe comprising a treatment module operable to be heated by Joule-Thomson heating; and a gas supply operable to supply a mixture of cooling gas and heating gas, in selected proportions, to the treatment module.

The gas supply preferably comprises a processor operable to select proportions of heating and of cooling gas supplied to the treatment module according to an algorithm responsive to temperature data garnered by thermal sensors. The sensors may be positioned within the probe or among tissues of a patient.

According to yet an additional aspect of the present invention there is provided a cryoprobe operable to cool first tissues to cryoablation temperatures while heating second tissues. The cryoprobe may further comprise a first treatment module operable to cool the first tissues and a second treatment module operable to heat the second tissues. Preferably the first treatment module is also operable to heat tissues, and the second treatment module is also operable to cool tissues. Most preferably, both the first treatment module and the second treatment module are operable both to heat tissues and to cool tissues, and each of the first treatment module and the second treatment module is operable to be independently controlled in cooling and heating.

The first treatment module may be positioned laterally to the second treatment module, or positioned longitudinally to the second treatment module. The probe may further comprise a third treatment module operable to heat and to cool. The first, second, and third treatment nodes may be positioned longitudinally one to another. The heating may be Joule-Thomson heating and the cooling may be Joule-Thomson cooling.

According to still an additional aspect of the present invention there is provided a method for accurately delimited cryoablation of a target, comprising inserting into a patient a plurality of cryoprobes, each of the cryoprobes comprising at least one treatment module and at least some of the cryoprobes comprising a plurality of treatment modules; positioning the cryoprobes so that a first plurality of the treatment modules are positioned within the target and a second plurality of the treatment modules are positioned exterior to, but adjacent to, the target; and warming the second plurality of treatment modules while cooling the first plurality of treatment modules to cryoablation temperatures, thereby creative a warming envelope around the target while cryoablating the target, thereby effecting accurately delimited cryoablation of the target. The method may further comprise utilizing imaging modalities to visual the target and the cryoprobes. The treatment modules of the first plurality of treatment modules may be cooled by Joule-Thomson cooling and treatment modules of the second plurality of treatment modules may be heated by Joule-Thomson heating, which may be provided by expansion of a mixture of cooling gas and heating gas.

According to a further aspect of the present invention there is provided a method for cryoablating a target while minimizing damage to tissues surrounding the target, comprising: introducing into the target a plurality of first treatment modules operable to perform cryogenic cooling; surrounding the target with a plurality of second treatment modules operable to heat tissues; utilizing the first treatment modules to cool tissues of the target to cryoablation temperatures; and utilizing the second treatment modules to heat tissues surrounding the target during cooling of the first treatment modules, thereby surrounding the target with an envelope of heated tissues during cryoablation of the target, thereby cryoablating the target while minimizing damage to tissues surrounding the target.

According to yet a further aspect of the present invention there is provided a method for accurately localizing a border of a cryoablation volume at a desired locus, comprising positioning a first treatment module within a cryoablation target; positioning a second treatment module in a vicinity of the first treatment module and outside the cryoablation target; determining or estimating distances of the first and the second treatment modules from the desired locus of a border of the cryoablation volume; calculating temperatures and durations for cooling of the first treatment module and for heating of the second treatment module, such as will create a cryoablation volume surrounding the first treatment module, which cryoablation volume will extend up to, and not beyond, the desired locus; and cooling the first treatment module and heating the second treatment module according to the calculated temperatures and durations, thereby creating a cryoablation volume having an accurately localized border positioned at the desired locus.

According to yet another aspect of the present invention there is provided a cryoprobe comprising an asymmetric tissue cooling module operable too cool tissues positioned in a first radial direction from the probe while protecting from cooling tissues positioned in a second radial direction from the probe.

Preferably, the cryoprobe comprises an inner cooling module and an exterior wall having first and second lateral portions, wherein only the first lateral portions of the exterior wall are joined to the inner cooling module by a heat-conducting segment. Alternatively or conjointly, the cryoprobe comprises an inner cooling module and an exterior wall, wherein a first lateral portion of the exterior wall is positioned touching the inner cooling module, and second lateral portions of the exterior wall are isolated from the inner cooling module by thermal insulation.

Preferably, the cryoprobe comprises thermal insulation between the inner cooling module and the second lateral portions of the exterior wall, which insulation may be a volume of air or a volume of at least partial vacuum. The probe may comprises a vacuum connector for connecting the cryoprobe to a vacuum pump for creating the at least partial vacuum, or it may comprises a venturi constriction and a pressure equalization passage fluidly connecting the venture constriction to a volume defined within external walls of the probe and external to an inner cooling module of the probe, such that low pressure generated in the constriction by acceleration therein of gas passing through the gas exhaust conduit induces suction which creates at least a partial vacuum in the volume.

According to preferred embodiments of the present invention the cryoprobe comprises an external wall having first and second lateral portions; a cooling module which produces a cold flowing fluid when the cryoprobe is operated in cooling, the cold flowing fluid being in direct contact with the first lateral portion of the external wall; and thermal insulation preventing contact between the cold flowing fluid and the second lateral portion of the external wall when the cryoprobe is operated in cooling. The cryoprobe preferably comprises a Joule-Thomson orifice and a gas exhaust lumen for exhausting gas cooled by expansion through the Joule-Thomson orifice, the gas exhaust lumen being in contact with the first lateral portion of the external wall. Preferably the cryoprobe further comprises a heat-exchanging configuration within the gas exhaust lumen, and thermal insulation positioned between the heat-exchanging configuration and the second lateral portion of the external wall.

According to additional preferred embodiments of the present invention, the cryoprobe comprises an external wall having first and second lateral portions; a cooling module which produces a cold flowing fluid when the cryoprobe is operated in cooling, the cold flowing fluid, when produced, being in direct contact with the first lateral portion of the external wall; and a fluid flow blocker serving to prevent the cold flowing fluid from flowing in contiguity to the second lateral portion of the external wall when the cryoprobe is operated in cooling. The probe may comprise a Joule-Thomson orifice, an expansion chamber, and an external wall, wherein the fluid flow blocker is a gas blocking element operable to prevent passage of gas exhausting from the expansion chamber from flowing along the second lateral portion of the exterior wall, thereby forcing the exhausting gas to flow along the first lateral portion of the exterior wall when the cryoprobe is active in cooling.

According to yet another aspect of the present invention there is provided a cryoprobe operable to be cooled by Joule-Thomson cooling, which cryoprobe comprises an insulation volume, a Joule-Thomson orifice, a gas input conduit for supplying a compressed gas to the Joule-Thomson orifice, and a gas exhaust conduit for exhausting gas decompressed by expansion through the Joule-Thomson orifice, wherein the gas exhaust conduit comprises a venturi constriction and a pressure equalization passage fluidly connecting the venturi constriction to the insulation volume, such that low pressure generated in the venturi constriction by acceleration therein of gas exhausting through the gas exhaust conduit induces suction which creates at least a partial vacuum in the insulation volume.

The present invention successfully addresses the shortcomings of the presently known configurations by providing an apparatus and method for cryoablation which results in a reduced volume of damaged tissue surrounding a selected cryoablation target, yet enables full and reliable cryoablation of that selected target. The method comprises establishing a protective envelope of gently heated tissue, formed to conform to the shape of at least a portion of a cryoablation target and positioned so as to at least partially surround that cryoablation target, while cryoablating that target, thereby substantially limiting tissue damage to the intended cryoablation target during cryoablation of that target.

The present invention further successfully addresses the shortcomings of the presently known configurations by providing an apparatus and method for cryosurgery enabling accurate delimitation of an ablation volume. The method comprises establishing a steep temperature gradient at the border of a cryoablation target, utilizing equipment visible to imaging modalities, thereby enabling a surgeon to directly observe the position of a sharply delimited border of a cryoablation operation in real time.

The present invention further successfully addresses the shortcomings of the presently known configurations by providing an apparatus and method for Joule-Thomson heating of a probe, which device and method provide heating to an upper limit of temperature, thereby protecting heated tissues from overheating, yet have a higher heating capacity than that provided by a Joule-Thomson probe heated by expansion of low-pressure helium gas.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
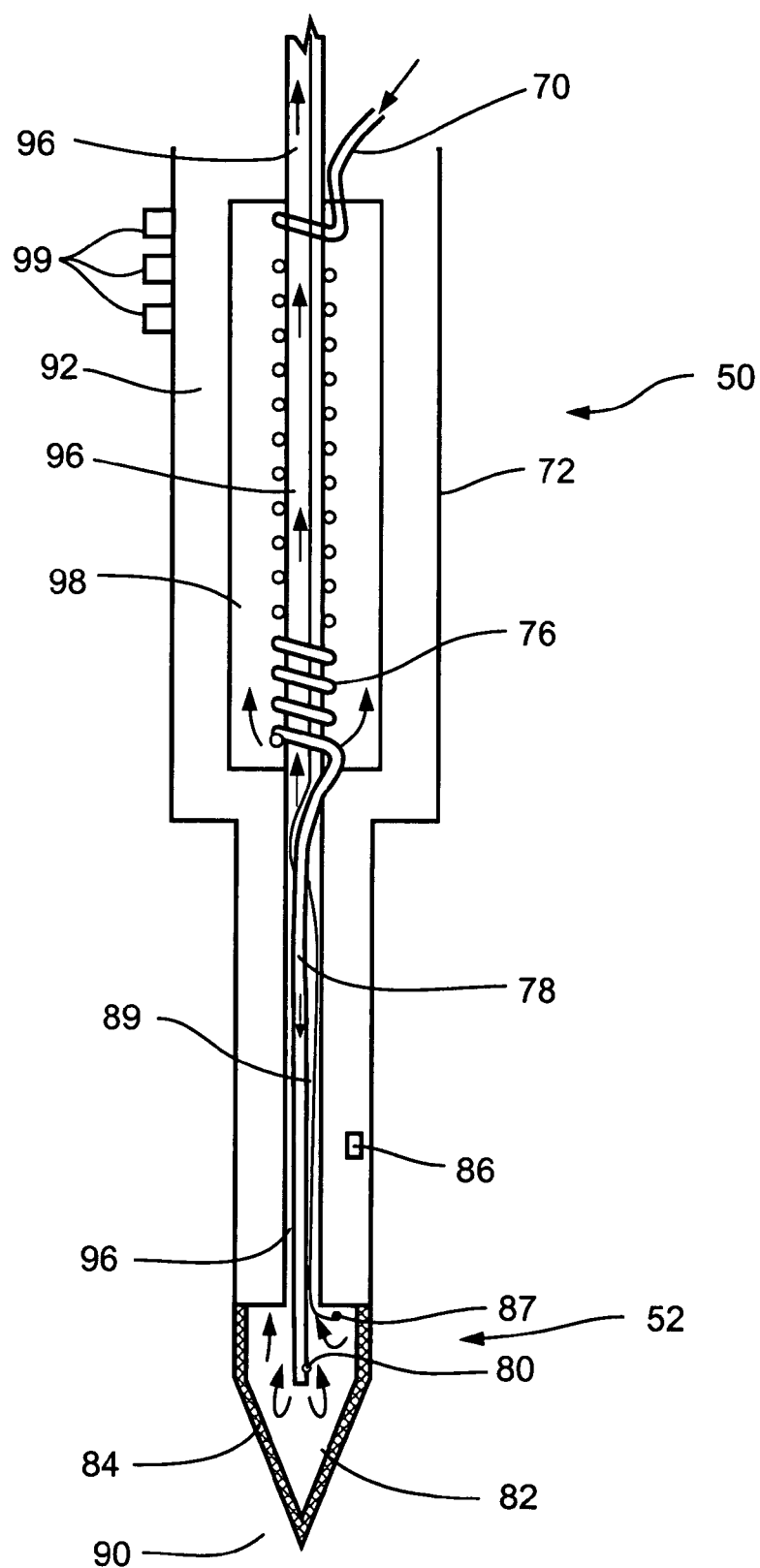
FIG. 1 is a simplified schematic of an exemplary cryoprobe, according to the methods of prior art.

The present invention relates to an apparatus and method for accurately delimited cryoablation of unwanted body tissues. More particularly, the present invention relates to method and apparatus for cryoablating a selected target volume of body tissue while surrounding or partially surrounding the target volume with a protective envelope of mildly heated tissue, so as to sharply delimit the volume of cryogenic destruction, minimize the volume of healthy tissue exterior to the selected cryoablation target which is damaged by the cryoablation process, and facilitate alignment, by a surgeon, of the borders of the sharply delimited actual volume of cryogenic ablation with the intended cryoablation target volume.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$, xenon, and $N_2O$, and various other gasses pass from a region of higher pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

The phrase "heating gasses" is used herein to refer to gasses which have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson cooler" is a Joule Thomson heat exchanger used for cooling. As used herein, a "Joule Thomson heater" is a Joule Thomson heat exchanger used for heating.

The term "ablation temperature", as used herein, is the temperature at which cell functionality and structure are destroyed by cooling. Temperatures below approximately −40° C. are generally considered to be ablation temperatures.

The term "ablation target" or "cryoablation target" refers to the volume of tissue desired to be ablated.

The "ablation volume" or "actual ablation volume" is the volume of tissue actually ablated during a cryoablation procedure. This is the volume cooled by a functioning cryoprobe to cryoablation temperatures. Cellular structures within the ablation volume are functionally and structurally destroyed. It is a general goal of cryoablative surgery that the actual ablation volume correspond, as closely as possible, to the intended cryoablation target.

The "damage envelope", as that term is used herein, is a volume of tissue, surrounding an ablation volume, within which structure and functionality of healthy tissues are damaged by a cryoablative procedure.

In discussion of the various figures described hereinbelow, like numbers refer to like parts.

For purposes of better understanding the present invention, as illustrated in FIGS. 8-21 of the drawings, reference is first made to the construction and operation of conventional (i.e., prior art) cryosurgery apparatus and treatment method as illustrated in FIGS. 1-7.

Figure 2:
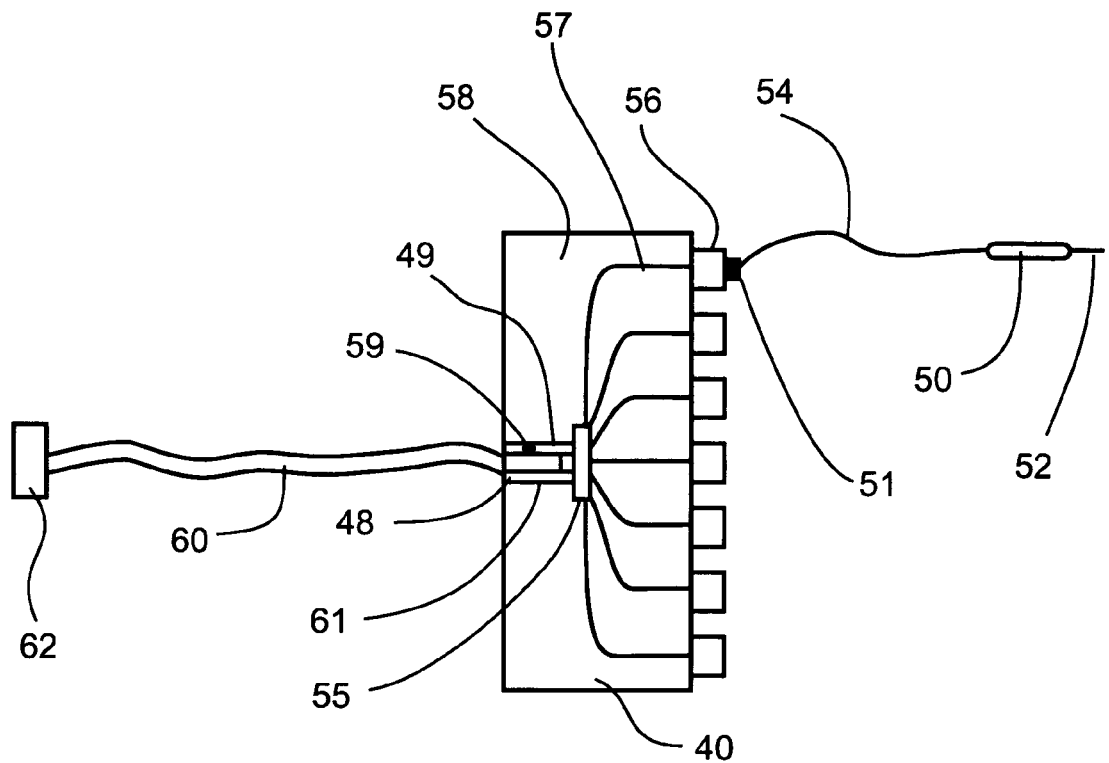
FIG. 2 is a simplified schematic of a manifold structure connecting a plurality of cryosurgical probes to a common gas source, according to the methods of prior art.
Figure 3:
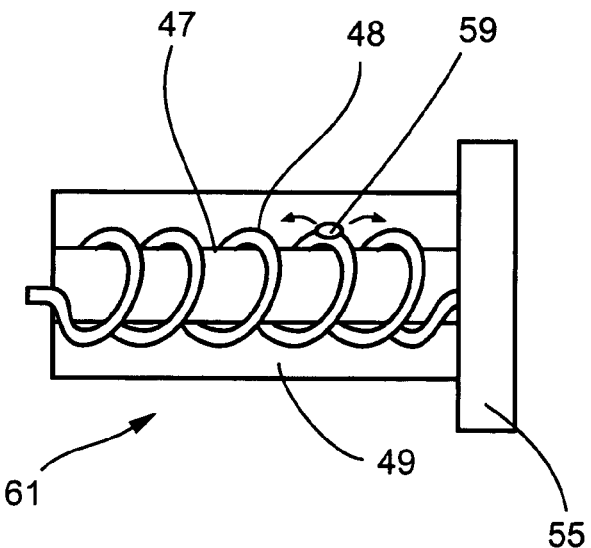
FIG. 3 is a simplified schematic of an alternative configuration of a pre-cooling element, according to the methods of prior art.

Referring to FIGS. 1-3, a cryosurgical apparatus according to methods of prior art includes a plurality of cryosurgical probes.

FIG. 1 presents a simplified schematic of an exemplary cryoprobe, according to the methods of prior art.

FIG. 1 presents a cryoprobe 50 having an operating tip 52 including a Joule-Thomson cooler for freezing a patient's tissue and a holding member 72 for holding by a surgeon. As shown in FIG. 1, operating tip 52 includes at least one passageway 78 extending therethrough for providing gas of high pressure to orifice 80 located at the end of operating tip 52, orifice 80 being for passage of high pressure cooling gas therethrough, so as to cool operating tip 52 and produce an ice-ball at its end 90.

When a high pressure cooling gas such as argon expands through orifice 80 it may liquefy, so as to form a cryogenic pool within chamber 82 of operating tip 52, which cryogenic pool effectively cools surface 84 of operating tip 52. Surface 84 of operating tip 52 is preferably made of a heat conducting material such as metal so as to enable the formation of an ice-ball at end 90 thereof.

Alternatively, a high pressure heating gas such as helium may be used for heating operating tip 52 via a reverse Joule-Thomson process, so as to enable treatment by cycles of cooling-heating, and further for preventing sticking of the probe to the tissue when extracted from the patient's body, and to enable fast extraction when so desired.

When a high pressure heating gas such as helium expands through orifice 80 it heats chamber 82, thereby heating surface 84 of operating tip 52.

Operating tip 52 includes at least one evacuating passageway 96 extending therethrough for evacuating gas from operating tip 52 to the atmosphere.

As shown in FIG. 1, holding member 72 may include a heat exchanger for pre-cooling the gas flowing through passageway 78. Specifically, the upper portion of passageway 78 may be in the form of a spiral tube 76 wrapped around evacuating passageway 96, the spiral tube being accommodated within a chamber 98. Thus, gas evacuated through passageway 96 may pre-cool the incoming gas flowing through spiral tube 76.

As further shown in FIG. 1, holding member 72 may include an insulating body 92 for thermally insulating the heat exchanger from the external environment.

Furthermore, operating tip 52 may include at least one thermal sensor 87 for sensing the temperature within chamber 82, the wire 89 of which extending through evacuating passageway 96 or a dedicated passageway (not shown). Probe 50 may further comprise one or more external thermal sensors 86, preferably placed at some distance from operating tip 52, operable to report on temperatures induced in surrounding tissues by cooling of operating tip 52.

In addition, holding member 72 may include a plurality of switches 99 for manually controlling the operation of probe 50 by a surgeon. Such switches may provide functions such as on/off, heating, cooling, and predetermined cycles of heating and cooling by selectively and controllably communicating incoming passageway 70 with an appropriate external gas container including a cooling or a heating gas.

Attention is now drawn to FIG. 2, which presents a simplified schematic of a gas distribution module connecting a plurality of cryosurgical probes 50 to a common gas source, according to the methods of prior art.

FIG. 2 presents a gas distribution module 40, wherein each of cryosurgical probes 50 is connected via a flexible connecting line 54 to a connecting site 56 on a housing element 58, preferably by means of a linking element 51. Cryosurgical probes 50 may be detachably connected to connecting sites 56.

Preferably, evacuating passageway 96 extends through connecting line 54, such that the outgoing gas is evacuated through an opening located at linking element 51 or at any other suitable location, e.g., manifold 55, see below. Preferably, line 54 further includes electrical wires for providing electrical signals to the thermal sensor and switches (not shown).

Each of cryosurgical probes 50 is in fluid communication with a manifold 55 received within a housing 58, manifold 55 being for distributing the incoming high pressure gas via lines 57 to cryosurgical probes 50.

As shown, housing 58 is connected to a connector 62 via a flexible cable 60 including a gas tube (not shown), connector 62 being for connecting the apparatus to a high pressure gas source and an electrical source.

The apparatus further includes electrical wires (not shown) extending through cable 60 and housing 58 for providing electrical communication between the electrical source and cryosurgical probes 50.

Preferably, housing 58 includes a pre-cooling element, generally designated as 61, for pre-cooing the high pressure gas flowing to cryosurgical probes 50. Preferably, pre-cooling element 61 is a Joule-Thomson cooler, including a tubular member 48 received within a chamber 49, tubular member 48 including an orifice 59 for passage of high pressure gas therethrough, so as to cool chamber 49, thereby cooling the gas flowing through tubular member 48 into manifold 55.

Attention is now drawn to FIG. 3, which presents an alternative configuration of a pre-cooling element 61 according to the methods of prior art, wherein tubular member 48 is in the form of a spiral tube wrapped around a cylindrical element 47, so as to increase the area of contact between tubular member 48 and the cooling gas in chamber 49.

According to yet another configuration (not shown), housing 58 includes a first tubular member for supplying a first high pressure gas to manifold 55, and a second tubular member for supplying a second high pressure gas to pre-cooling element 61. Any combination of gases may be used for cooling and/or heating the gases flowing through such tubular members.

Alternatively, a cryogenic fluid such as liquid nitrogen may be used for pre-cooling the gas flowing through housing 58. Alternatively, an electrical pre-cooling element may used for pre-cooling the gas.

Preferably, thermal sensors (not shown) may be located within cable 60 and manifold 55 for measuring the temperature of gas flowing therethrough.

Figure 4:
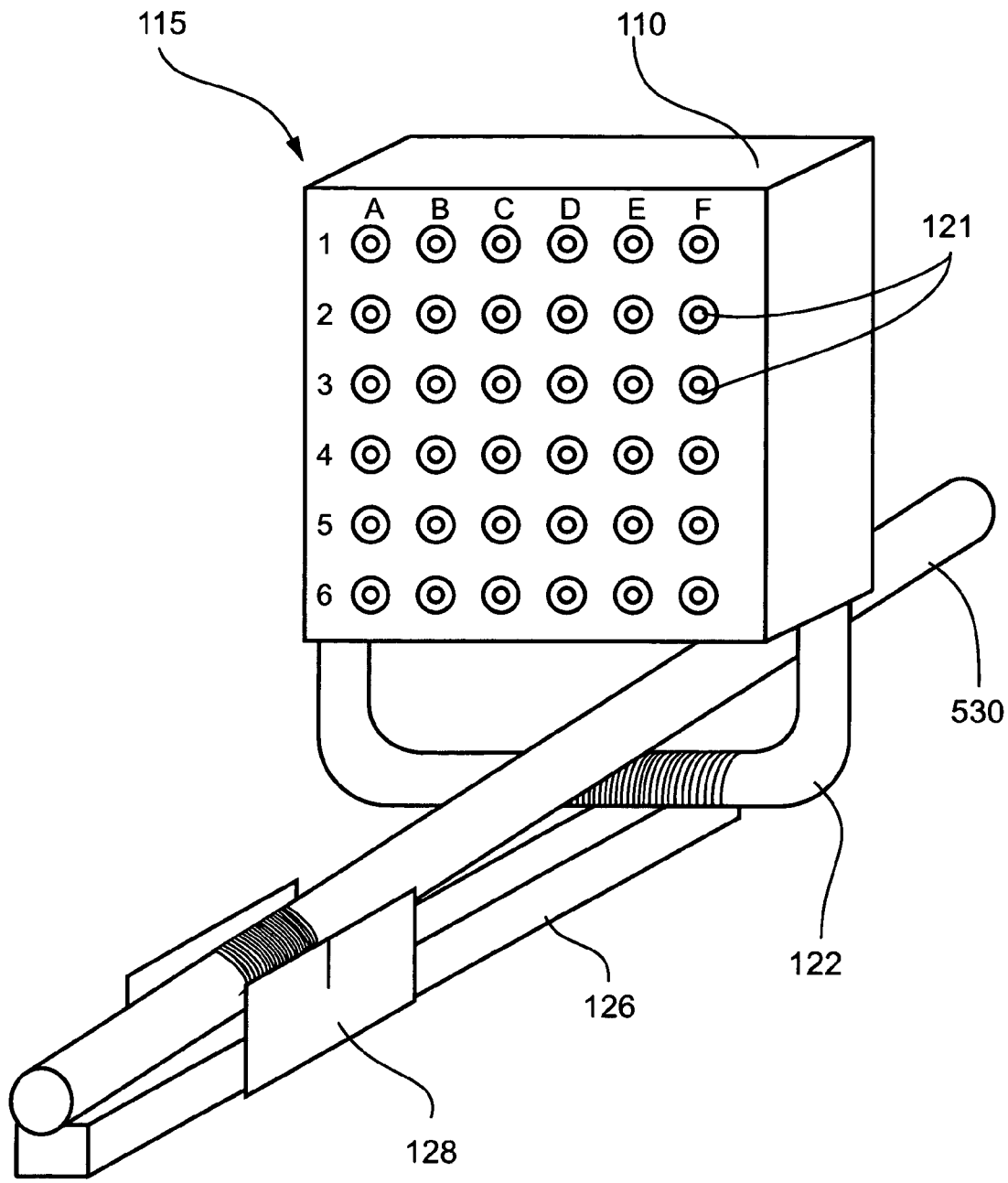
FIG. 4 is a simplified schematic of an apparatus comprising an ultrasound probe and a guiding element for guiding insertion of a plurality of cryoprobes into a patient's body, according to the methods of prior art.
Figure 5:
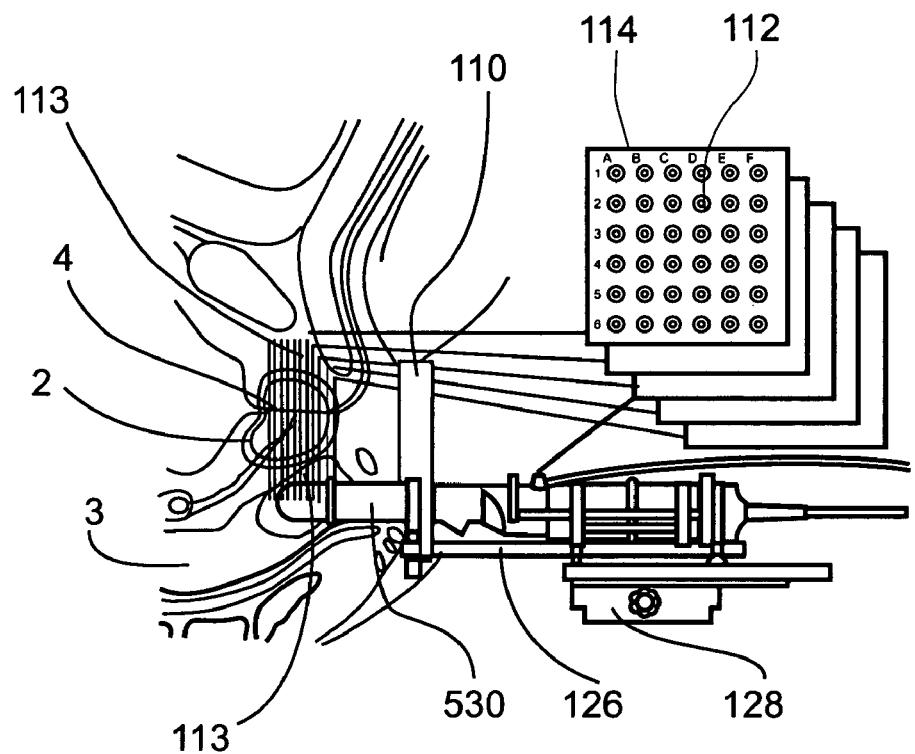
FIG. 5 is a simplified schematic showing a method of use of the apparatus presented in FIG. 4, according to the methods of prior art.
Figure 6:
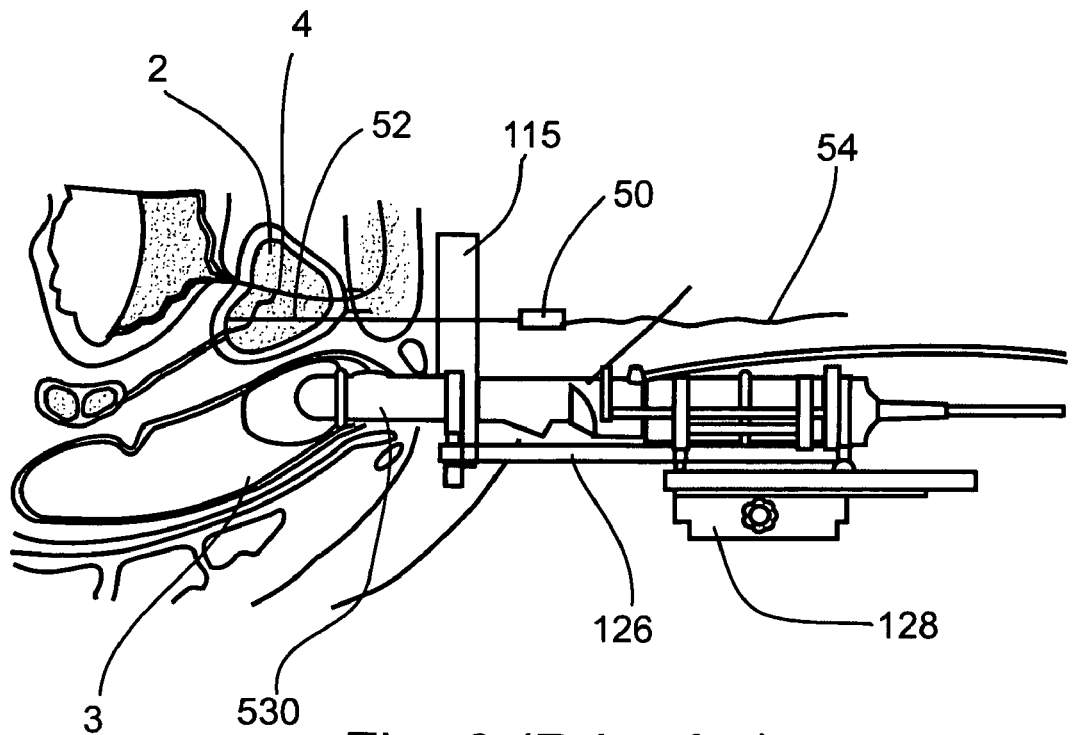
FIG. 6 is a simplified schematic showing a further step in the use of the apparatus presented in FIG. 4, according to the methods of prior art.

Attention is now drawn to FIGS. 4-6, which present a prior art method and apparatus utilizing an imaging device to form a three-dimensional grid of the patient's treated organ, e.g., prostate, the three dimensional grid serves for providing information on the three dimensional shape of the organ. Each of a set of cryosurgical probes is then inserted to a specific depth within the organ according to the information provided by the grid.

FIG. 4 is a simplified schematic of an apparatus comprising an ultrasound probe and a guiding element for guiding insertion of a plurality of cryoprobes into a patient's body, according to the methods of prior art. The example given is of an apparatus adapted for cryoablation of a prostate.

As shown in FIG. 4, an ultrasound probe 530 is provided for insertion into the patient's rectum, ultrasound probe 530 being received within a housing element 128. A guiding element 115 is connected to housing element 128 by means of a connecting arm 126. As shown, guiding element 115 is in the form of a plate 110 (also called a "guide 110" or a "template 110") having an array or net of apertures 121, each aperture serves for insertion of a cryosurgical probe therethrough. Preferably, the distance between each pair of adjacent apertures 121 is between about 2 millimeters and about 5 millimeters.

Attention is now drawn to FIG. 5, which is a simplified schematic showing a method of use of the apparatus presented in FIG. 4.

As shown in FIG. 5, ultrasound probe 530 is introduced to a specific depth 113 within the patient's rectum 3. A net of marks 112 is provided on the obtained ultrasound image 114, the net of marks 112 on image 114 being accurately correlated to the net of apertures 121 on guiding element 115.

Thus, marks 112 on image 114 sign the exact locations of the centers of ice-balls which may be formed at the end of the cryosurgical probes inserted through apertures 121 to the patient's prostate 2, wherein image 114 relates to a specific depth of penetration 113 of the cryosurgical probes into the prostate 2.

As shown in FIG. 5, ultrasound probe 530 is gradually introduced to various depths 113 of rectum 3, thereby producing a set of images 114, wherein each image relates to a respective depth of penetration into the prostate 2. Thus, each of images 114 relates to a specific plane perpendicular to the axis of penetration of the cryosurgical probes.

The set of images 114 provides a three dimensional grid of the prostate. Such three-dimensional grid is then used for planning the cryosurgical procedure.

For example, the introduction of a cryosurgical probe along a given axis of penetration to a first depth may effectively destroy a prostatic tissue segment, while introduction of the probe to a second depth may severely damage the prostatic urethra.

Since the ice-ball is locally formed at the end of the cryosurgical probe, each probe may be introduced to a specific depth so as to locally provide an effective treatment to a limited portion of the prostate while avoiding the damaging of non-prostatic or prostatic tissues located at other depths of penetration.

Attention is now drawn to FIG. 6, which is a simplified schematic presenting a further step in the use of the apparatus presented in FIG. 4, according to the methods of prior art.

FIG. 6 shows the insertion of an operating tip 52 of a cryosurgical probe 50 through an aperture of guiding element 115 into the prostate 2 of a patient.

Preferably, a plurality of cryosurgical probes are sequentially inserted through apertures 121 of guiding element 115 into the patient's prostate, wherein each probe is introduced to a specific depth, thereby providing substantially local effective treatment to distinct segments of the prostatic tissue while avoiding the damaging of other prostatic or non-prostatic tissue segments.

Preferably, each of the cryosurgical probes includes a scale for indicating the depth of penetration into the prostate.

Thus, it may be seen that the prior art apparatus and methods presented by FIGS. 1-6 enable diagnostic mapping of areas to be treated within a prostate, and further enable guiding a plurality of cryogenic probes into a prostate in such a manner that the cryogenic probes are placed according to the planned treatment areas so mapped. It will be clear to one skilled in the art that the prior art methods presented by FIGS. 1-6 may be adapted, with appropriate modifications, to cryoablation of various other organs of the body.

Figure 7A:
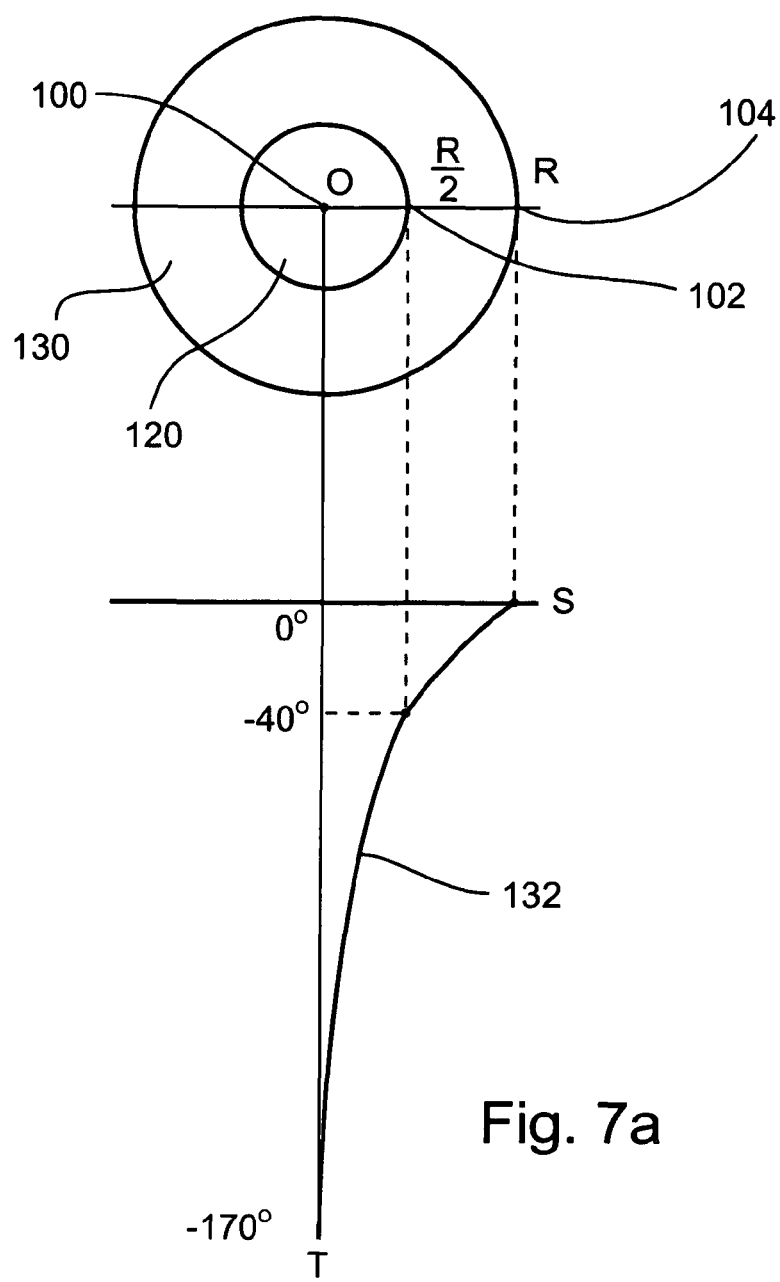
FIG. 7A is a graph showing the profile of temperature distribution within an ice-ball formed at the tip of a cryosurgical probe.

Attention is now drawn to FIG. 7A, which is an illustration of the profile of temperature distribution across an ice-ball formed at the tip of a cryosurgical probe. As shown, the temperature at a surface 104 of the ice-ball is 0° C. The temperature declines exponentially towards a cooled center 100 of the ball where it preferably reaches the value of −170° C., such that an isothermal surface 102 of about −40° C. is typically located within the ice-ball approximately half way between the center of the ball and its outer surface 104. Thus, if the ice-ball features a radius R, then the radius of the −40° C. isothermal surface 102 is about R/2. The tissue volume contained within isothermal surface 102 generally corresponds to the "ablation volume" defined hereinabove.

Figure 7B:
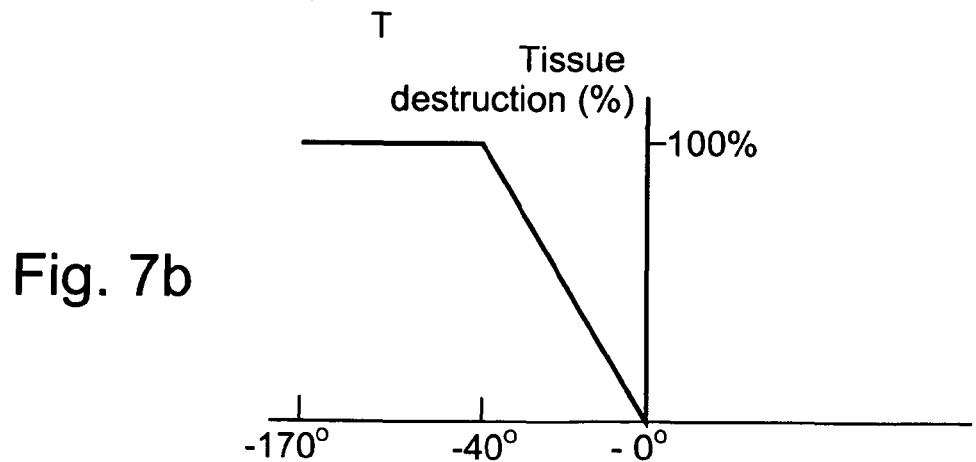
FIG. 7B is a graph showing the effectiveness of a cryosurgical treatment, given in percentage of tissue destruction, as a function of temperature.

Attention is now drawn to FIG. 7B, which is a graph showing the effectiveness of a cryosurgical treatment (given in percentage of tissue destruction) as a function of temperature. As shown, the temperature required for effectively destroying a tissue is at least about −40° C. Accordingly, in order to effectively destroy a tissue, the isothermal surface of −40° C. (marked as surface 102 in FIG. 1A) should be placed at the periphery of the treated tissue so that the entire volume of the treated tissue is exposed to cryoablation temperatures, temperatures at or below −40° C.

FIGS. 7A and 7B together illustrate the fact that that when a volume of tissue is treated by being exposed to cryoablation temperatures, that volume is enveloped by a second volume of tissues, termed the "damage envelope" herein, wherein healthy tissues and organs exposed to the external portion of the ice-ball are subject to temperatures of between about −40° C. and 0° C.

Thus, the "ablation volume" 120 shown in FIG. 7A approximately corresponds to the volume of tissues contained within surface 102, and the "damage envelope" 130 shown in FIG. 7A approximately corresponds to the volume of tissue between the isotherm at −40° C., surface 102, and the isotherm at 0° C., surface 104, the surface of the ice ball. (In practice, exact dimensions and positioning of the actual ablation volume is dependent not only on temperature but also on duration of freezing, on freeze/thaw cycles, etc.)

FIG. 7B makes it clear that tissues cooled to between 0° C. and −40° C. are subject to damage, which damage may result in necrosis of healthy tissue and in temporary or permanent impairment of the function of otherwise healthy organs.

Preferred embodiments of the present invention may now be described, utilizing the exemplary context of the prior art apparatus and methods described hereinabove and presented in FIGS. 1-7. It is noted, however, that the aforementioned prior art context is here described for exemplary purposes only. The invention disclosed herein is not limited to the exemplary context. In particular, alternative methods of diagnostic mapping may be utilized, such as x-ray mapping, CT mapping with or without use of a contrast medium, MRI mapping, ultrasound mapping not utilizing the anal probe described above, and others. Cryoprobes dissimilar to cryoprobe 50 presented in FIG. 1 may be utilized in embodiments of the present invention, on condition that they are capable of cooling tissues to cryoablation temperatures. Apparatus and methods other than those depicted in FIGS. 3-6 may be utilized to accurately deliver one or more cryoprobes to a selected locus for cryoablation of tissues thereat, and to accurately deliver one or more heating probes to selected locations, as will be explained hereinbelow.

Figure 8A:
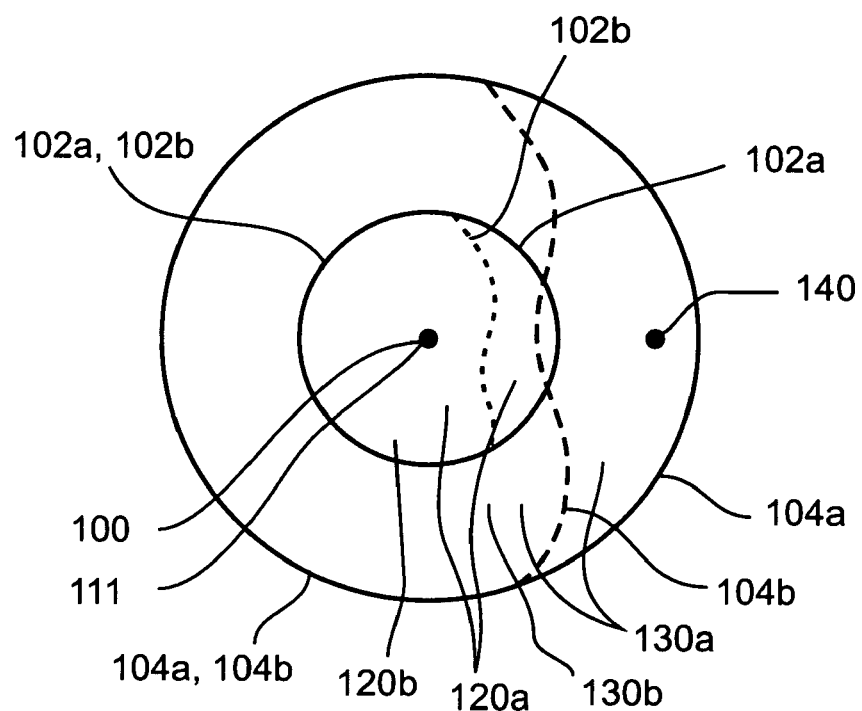
FIG. 8A is a simplified graph showing effects of cryosurgical cooling at a selected site together with mild heating of an adjacent site, according to an embodiment of the present invention.

Attention is now drawn to FIG. 8A, which is a simplified graph showing effects at a cryoablation site when cryosurgical cooling is combined with mild heating of tissues at an adjacent site. Cold source 100, which may be a cryoprobe 111 functional in cooling, creates an ablation volume 120 surrounded by a damage envelope 130. The isothermal surface 102A marks the limit of ablation volume 120A, which is the ablation volume produced when cold source 100 is cooled to cryoablation temperatures, and no heating is used. Thus, ablation volume 120A presents a shape similar to the shape presented as ablation volume 120 in FIG. 7A.

When a heat source 140 is utilized in conjunction with cooling source 100, tissues in their vicinity will be cooled by cooling source 100 and heated by heating source 140. Consequently, the temperature of such tissues will be a function of their distance from both cooling source 100 and heating source 140, and of the temperature of those two sources over time. Isothermal line 102B shows, in approximate form, a shape of an ablation volume under the influence of heat source 140 as well as of cold source 100. Ablation volume 120B may be seen to be flattened on the side exposed to heat source 140.

Similarly, isothermal surface 104A shows the outer border of damage envelope 130A when cold source 100 is activated and heat source 140 is inactive, and consequently resembles the shape of damage envelope 130 portrayed in FIG. 7A. Isothermal surface 104B shows, in approximate form, a shape of an outer border of a damage envelope 130B under the influence of heat source 140 as well as of cold source 100. Damage envelope 130B may be seen to be flattened on the side exposed to heat source 140.

It is further noted that distance between cold source 100 and the border of ablation volume 120A is smaller than the distance between cold source 100 and the border of ablation volume 120B, on the side facing heat source 140. In other words, ablation volume 120B, with heating, is considerably thinner than ablation volume 120A, without heating.

Similarly, it is further noted that the distance between isothermal surface 102B and isothermal surface 104B is also considerably smaller than the distance between isothermal surface 102A and isothermal surface 104A. Isothermal surface 102B is the internal border of damage envelope 130B, and isothermal surface 104B is its external border, while isothermal surface 102A is the internal border of damage envelope 130A, and isothermal surface 104A is its external border. Thus, damage envelope 130B, under heating, is considerably thinner than damage envelope 130A, absent heating, on the side of heater 140.

Figure 8B:
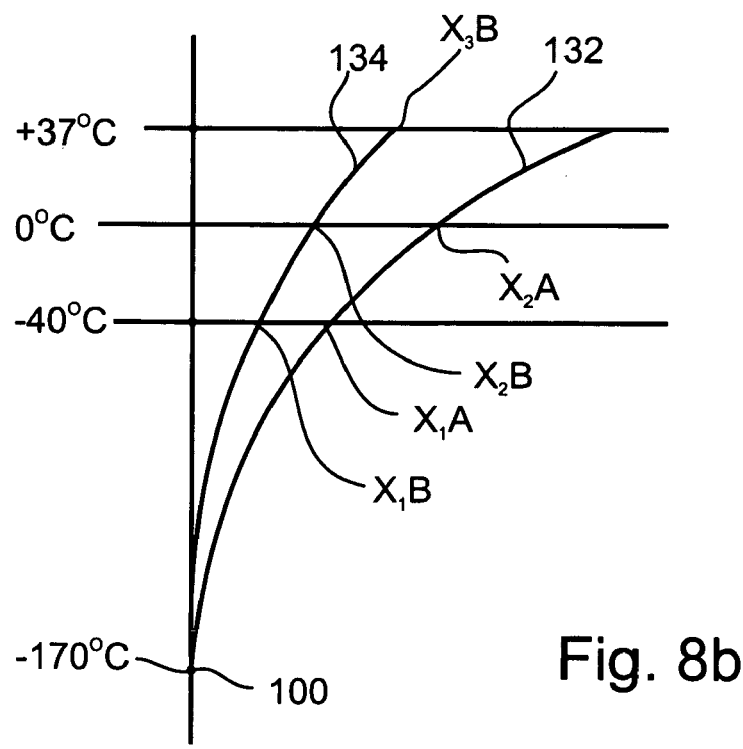
FIG. 8B is a simplified graph showing a steep temperature gradient produced when cryogenic cooling is associated with mild heating of an adjacent site, according to an embodiment of the present invention.

Attention is now drawn to FIG. 8B, which is a simplified graph showing a steep temperature gradient produced when cryogenic cooling at a first site is associated with mild heating of a second, adjacent, site, according to an embodiment of the present invention.

Gradient 132 of FIG. 8B reproduces gradient 132 of FIG. 7A. (The scale of FIG. 8B has been expanded somewhat, in the horizontal direction, for clarity of the image.) Thus, gradient 132 depicts a rise in temperature as an exponential function of distance from a center of cooling 100. Point X1A is the intersection of that gradient with the −40° C. isotherm, and point X1B is the intersection of that gradient with the 0° C. isotherm. Thus, cooling center 100 is taken to be the origin of the graph, X1A is the distance from the center of cooling to the border of an ablation volume, and (X2A−X1A) is the thickness of the damage envelope, corresponding to the distance between points 102 and 104 of FIG. 7A.

Gradient 134, in FIG. 8B, represents a temperature gradient produced when a heating element such as heater 140 of FIG. 8A is operated in conjunction with cryogenic cooling. If a heater 140 is operated at a distance X3B from cooling center 100, a gradient similar to gradient 134 will be produced. As may be observed from inspection of FIG. 8B, gradient 134 is such that the indicated thickness of the damage envelope (X2B−X1B) is much reduced in comparison to that produced by gradient 132 (without associated heating), and the distance from center of cooling 100 to the border of the ablation volume is also much reduced when compared to that produced by gradient 132. That is, ((X2A−X1A)>(X2B−X1B)), and (X1A>X1B).

The distance of heater 140 from cooler 100 is arbitrarily placed at position X3B, yet it will be appreciated that as X3B is moved closer to the X=0 position, gradient 134 becomes correspondingly steeper, and the distances X1B (radius of the ablation volume at that point) and (X2B–X1B), thickness of the damage envelope at that point, are correspondingly reduced. In other words, within certain practical limits, by proper placement of a warming source 140 in a vicinity of a cooling source 100, gradient 134 can be made to approximate a step-wise temperature change, and distances X1B and (X2B–X1B) can be substantially reduced, when compared to distances X1A and (X2A–X1A) of the prior art gradient 132 shown in FIGS. 7A and 8B.

Figure 9:
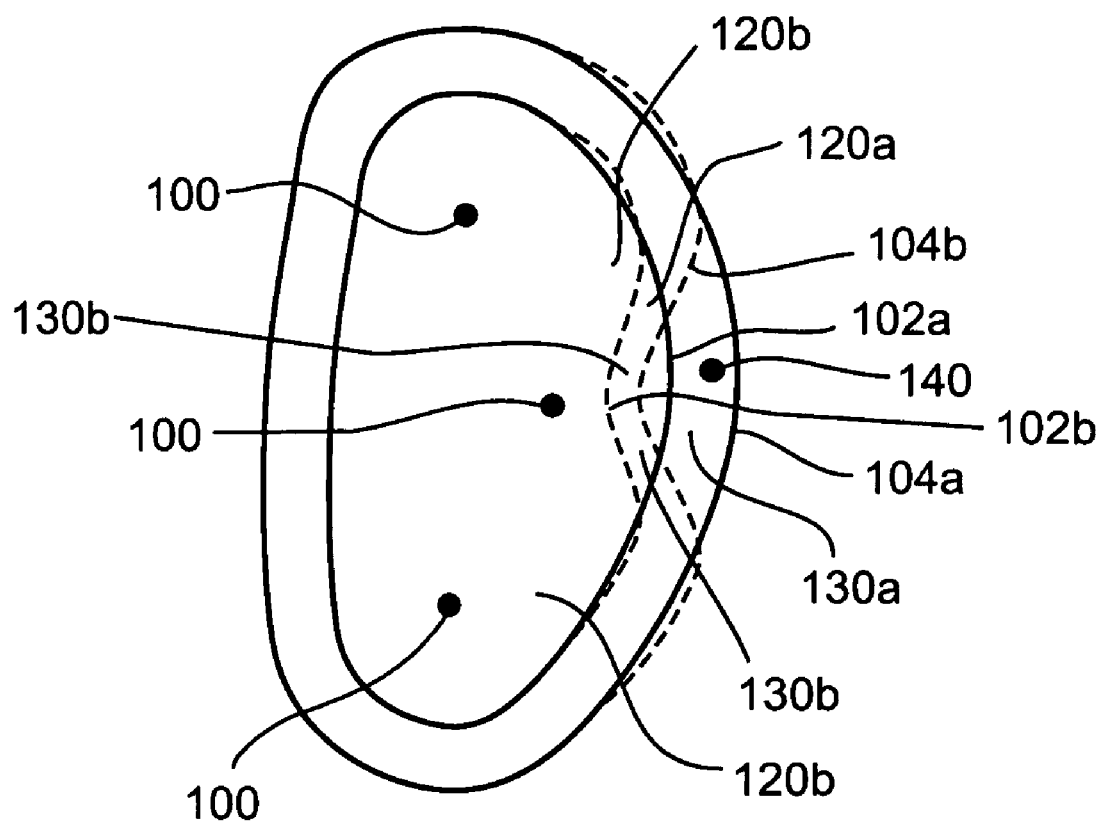
FIG. 9 is a simplified graph showing effects of cryosurgical cooling at three selected sites, together with mild heating at an adjacent site, according to an embodiment of the present invention.
Figure 10:
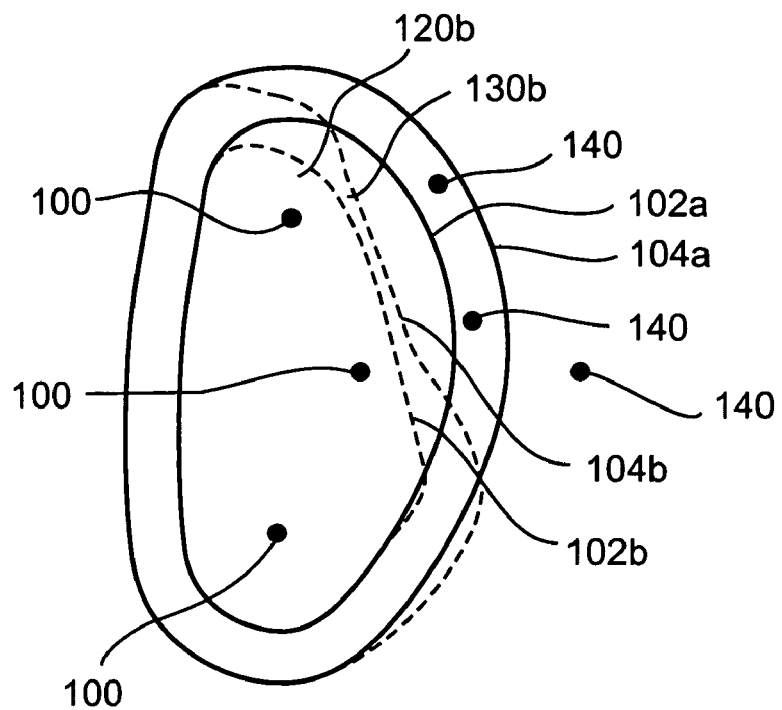
FIG. 10 is a simplified graph showing effects of cryosurgical cooling at three selected sites, together with mild heating at three adjacent sites, according to an embodiment of the present invention.
Figure 11:
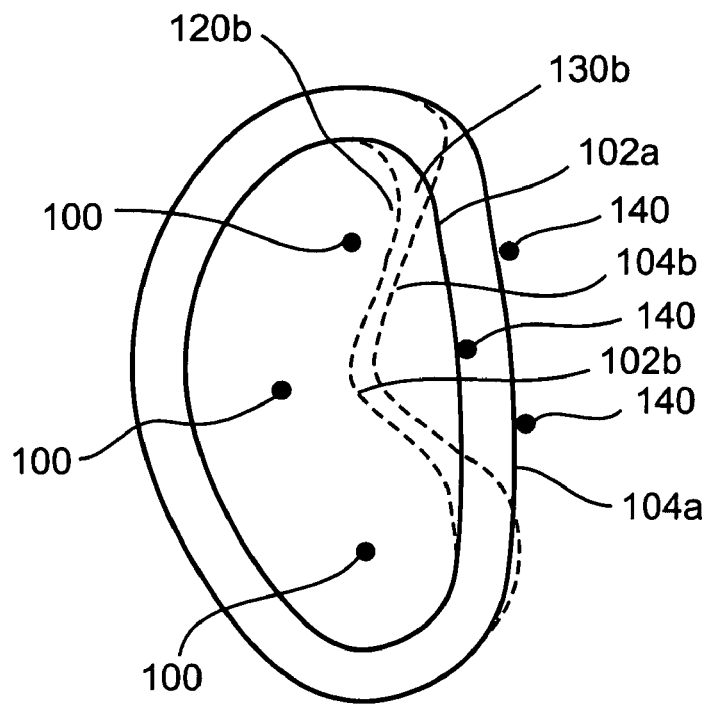
FIG. 11 is another simplified graph showing effects of cryosurgical cooling at three selected sites, together with mild heating at three adjacent sites, according to an embodiment of the present invention.

Attention is now drawn to FIGS. 9-11, which together demonstrate that combinations of cooling probes and heating probes, placed in selected positions and cooled to selected temperatures at selected times, are operable to create a combined ablation volume whose shape may be crafted to substantially conform to a three-dimensional shape of a desired cryoablation target such as a particularly shaped organ or tumor.

FIG. 9 is a simplified graph showing effects of cryosurgical cooling at three selected sites, together with mild heating at a single adjacent site, according to an embodiment of the present invention. In FIG. 9, isotherms 102A and 104A, shown as solid lines, represent isothermal surfaces at −40° C. and 0° C., respectively, expected to obtain under cryogenic cooling at the three depicted cooling sites 100, in the absence of heating at heating site 140. Isotherm 102A constitutes an outer border of ablation volume 120A, and an inner border of damage envelope 130A, whose outer border is isotherm 104A.

In FIG. 9, as in FIG. 8A, broken lines are used to show isotherms 102B and 104B, representing isothermal surfaces at −40° C. and 0° C., respectively, obtained when cooling at the depicted cooling sites 100 is accompanied by heating at heating site 140. Isotherm 102B constitutes an outer border of ablation volume 120B, obtained when cooling at sites 100 is accompanied by heating at site 140. Damage envelope 130B, similarly obtained during cooling at sites 100 while heating at site 140, has an inner border formed by −40° C. isotherm 102B, and an outer border formed by 0° C. isotherm 104B. As may be seen from inspection of FIG. 9, heating at heater 140 during cooling at sites 100 has an effect of indenting the ablation volume in a vicinity of site 140, and of reducing the thickness of damage envelope 130B in that vicinity.

Attention is now drawn to FIGS. 10 and 11, which are simplified graphs showing effects of cryosurgical cooling at three selected sites, together with mild heating at three adjacent sites, according to an embodiment of the present invention.

FIGS. 10 and 11 are similar to FIG. 9, except that whereas only one heating site 140 was presented in FIG. 9, three heating sites 140 are presented in FIGS. 10 and 11, with consequent modification of the size and shape of ablation volumes 120B, and damage envelopes 130B, as shown.

It may be appreciated from inspection of FIG. 10 that appropriate placement of sites 100 for cooling and of sites 140 for heating enables to obtain an ablation volume border 102B which is substantially straight along a substantial segment, and which is relatively close to cooling sites 100. It may be similarly appreciated from inspection of FIG. 11 that an alternative placement of cooling sites 100 and of heating sites 140 produces an ablation volume border indented almost 90°, and having a damage envelope which is extremely thin in that region.

Collectively, FIGS. 9-11 demonstrate that use of a plurality of cooling cryoprobes in a first selected configuration, together with use of a plurality of heating probes proximate to those cooling probes and in a second selected configuration, enables to craft an ablation volume 120B having a border which conforms to a desired three-dimensional shape, which border may be crafted to substantially conform to size and three-dimensional shape of a desired cryoablation target.

Various benefits are thereby obtained. Two benefits, already discussed hereinabove, are: (i) substantially limiting cryoablation to a desired cryoablation target; and (ii) significantly reducing the thickness of a damage envelope surrounding a cryoablation volume A third benefit is now noted, and its significance explained. FIGS. 10 and 11 demonstrate, in a general manner, the fact that use of a plurality of heating sites in conjunction to a plurality of cooling sites can have the effect of moving isotherm 102B, the outer border of cryoablation volume 120B, relatively close to each of a plurality of cooling probes 111 or other cooling sites 100.

An important advantage is thereby obtained. As discussed in the background section hereinabove, one significant problem associated with cryoablation procedures known to prior art is that border 102 of a cryoablation volume 120 is not directly visible under known imaging modalities. Ultrasound, for example, can easily render visible border 104, the 0° C. isothermal surface, corresponding to the edge of an ice ball of frozen tissue, yet the significant isotherm 102, border of the area within which tissues are reliably cryoablated, is not directly visible, and its presence and position must be calculated or guessed or inferred from such known facts as the position of border 104.

This prior art limitation is significantly alleviated under the conditions shown, by way of example, in FIGS. 10 and 11. Both probes 111 at sites 100, and border 104B, the edge of an iceball formed during cryoablation, may be rendered visible by use of appropriate imaging modalities or combinations of imaging modalities such as ultrasound, fluoroscope, or MRI. When the distance between probes 111 and border 104 is great, the position of border 102, somewhere between probes 111 and border 104, can only be approximately inferred. When, however, the distance between probes 111 and border 104 is substantially reduced, as shown in FIGS. 10 and 11, then an operator's uncertainty as to the exact position of border 102, the cryoablation volume border, is reduced proportionally.

As shown schematically by FIGS. 8B, 9, 10, and 11, appropriate selection and placement of a plurality of heating sites in proximity to a plurality of cooling sites can have the effect of producing a steep temperature gradient, approximating a step-wise reduction in temperature, at a selected shaped three-dimensional locus. Thus, not only can such a locus be designed and caused to conform to a three-dimensional shape of a cryoablation target, but the effective border of the resultant cryoablation volume can be caused to be close both to the heating and to the cooling probes employed, and be close to the edge of an iceball created during cryoablation. Yet, heating probes, cooling probes, and the iceball edge may all be visible under ultrasound and other imaging modalities. Thus, using the technique here described, an operator can not only design a refined three-dimensionally shaped cryoablation volume, but he can also "see" where his ablation intervention is actually taking place, in real time.

Figure 12:
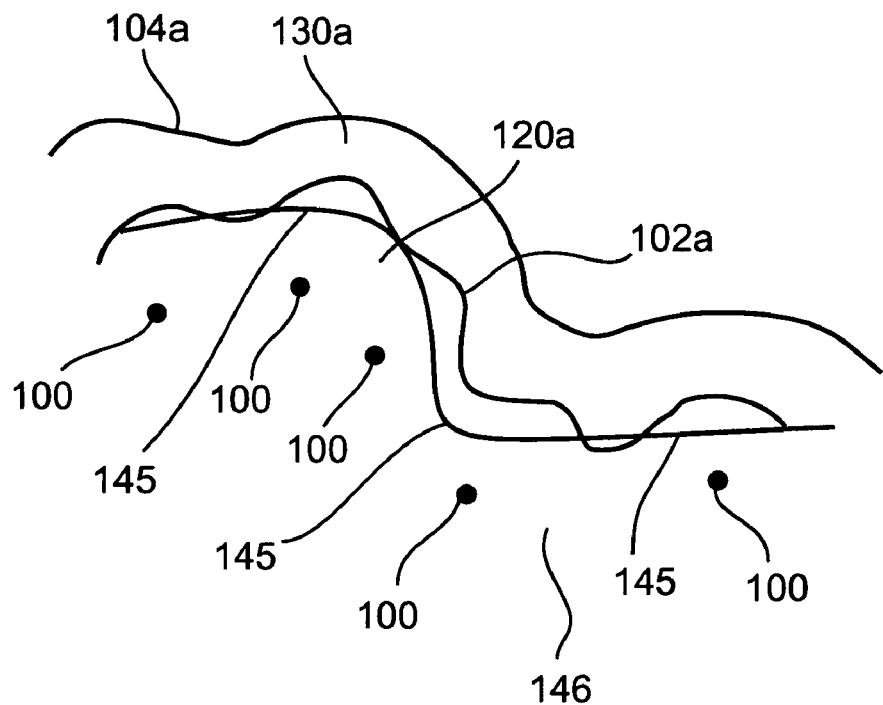
FIG. 12 is a simplified graph comparing the border of a damage envelope to a border of a cryoablation target, according to methods of prior art.

Attention is now drawn to FIGS. 12, which is a simplified graph comparing a border of a damage envelope to a border of a cryoablation target, according to methods of prior art. It is to be contrasted with FIG. 13, which presents a simplified graph comparing the border of a damage envelope to a border of a cryoablation target, according to an embodiment of the present invention.

In FIG. 12, line 145 represents a border of a desired cryoablation target 146. A plurality of cryoprobes or other cooling sources 100 are placed within cryoablation target 145, and cooled to create an ablation volume 120A having a border 102A, and a damage envelope 130A having an external border 104A. FIG. 12 represents what might generally be considered a reasonably good fit of ablation volume 120A to target border 145, according to methods of prior art.

Figure 13:
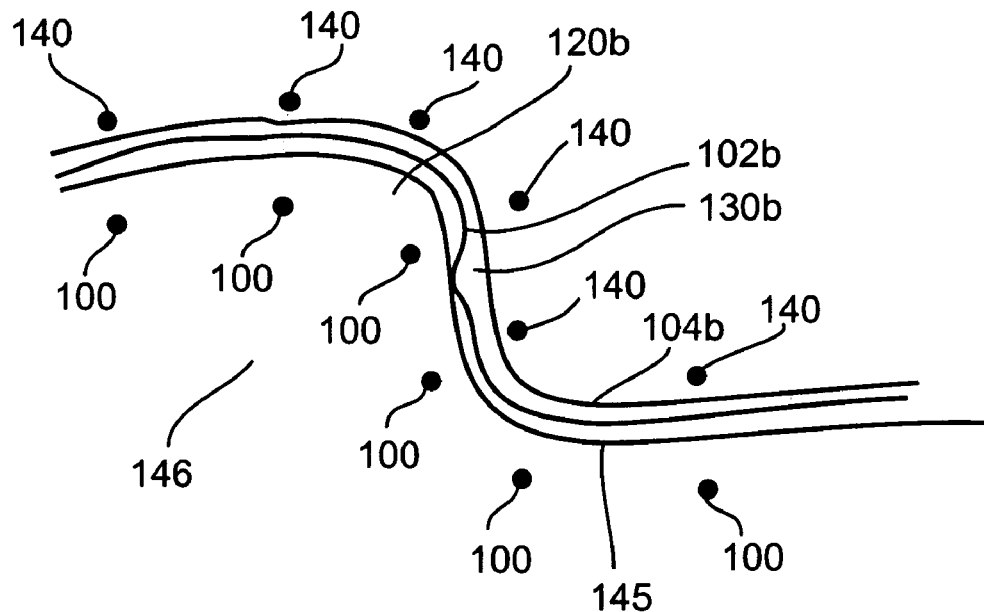
FIG. 13 is a simplified graph comparing the border of a damage envelope to a border of a cryoablation target, according to an embodiment of the present invention.

FIG. 12 may be contrasted to FIG. 13, which presents a simplified graph comparing a border of a damage envelope to a border of a cryoablation target, according to an embodiment of the present invention. In FIG. 13, a plurality of heating probes 140 are placed in proximity to a plurality of cooling probes 100, and heating probes 140 are heated during cooling of cooling probes 100. Border 102B is an approximate rendition of a border of an ablation volume 120B, and border 104B is an approximate rendition of an exterior border of a damage envelope 130B.

Close proximity of heating probes 140 to cooling probes 100 effects a steep temperature gradient between each cooling probe 100 and a nearby heating probe 140. The resultant steep gradient enables placement of probes 100 relatively near to target border 145, and has an effect of compressing damage envelope 130B into a relatively thin envelope, when compared to damage envelope 130A presented in FIG. 12. Thus, accuracy of ablation of target 146 is enhanced, and damage to tissues exterior to target 146 is minimized.

In a preferred embodiment of the present invention, the principles discussed with reference to FIGS. 8-13 above are implemented utilizing the prior art apparatus described hereinabove with particular reference to FIGS. 4, 5, and 6. Thus, that prior art apparatus may be adapted to a new utilization in the context of embodiments of the present invention.

Generally speaking, the method of the present invention requires locating (typically, by use of imaging modalities) a cryoablation target in three-dimensional space, then utilizing a probe placement mechanism to place a plurality of cooling cryoprobes within that cryoablation target, and also to place a plurality of heating probes partially surrounding, and preferably completely surrounding, that cryoablation target, then heating those heating probes while cooling those cooling probes to accurately cryoablate the target.

The apparatus and method described hereinabove with particular reference to FIGS. 4, 5, and 6, may be used for this purpose. One might, for example, utilize ultrasound probe 130 (FIG. 4) to gather information enabling three-dimensional mapping of a cryoablation target such as a tumor. Guiding template 110 may then be used to guide cooling and heating probes to appropriate positions in three-dimensional space, in accordance with the treatment strategies described herein. In particular, template 110 is operable to guide placement in three dimensions of both heating and cooling probes.

Figure 14:
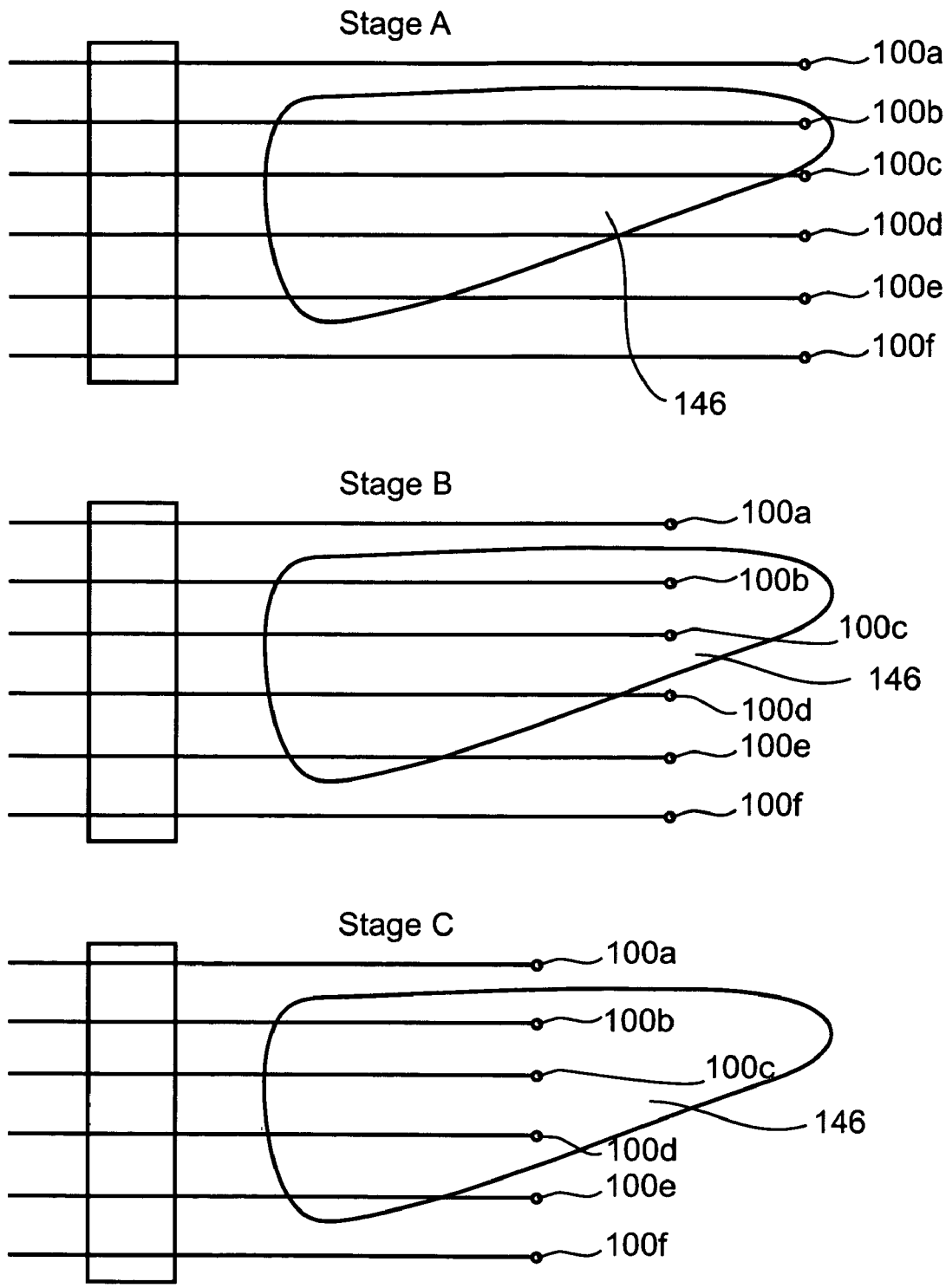
FIG. 14 is a simplified schematic of three stages in a procedure for cryoablation of a target, according to an embodiment of the present invention, with emphasis on treatment of lateral borders of a target.

Attention is now drawn to FIG. 14, which is a simplified schematic of three stages in a procedure for cryoablation of a target, with emphasis on treatment of lateral borders of that target, according to an embodiment of the present invention.

FIG. 14 presents what is termed in the art a "pull-back" procedure: a plurality of cryoprobes, labeled 100A-100F, operable both to heat and to cool, are passed through template 110, into the body of a patient, both into and around a cryoablation target 146 previously identified and localized using imaging modalities such as ultrasound probe 130 or other well-known diagnostic tools. As is well known in the art, a pull-back procedure involves ablating target 146 in several stages. Typically, a plurality of cryoprobes is introduced into a target, such as a prostate, at a selected depth, those cryoprobes are cooled to cryoablation temperatures, then preferably heated to free the probes from adhesion to frozen tissue. The probes are then typically withdrawn to a lesser depth of penetration, whereupon they are again cooled to ablate an additional layer of target 146, and so on, for as many iterations as necessary to treat the entire target.

According to a preferred embodiment of the present invention, cryoprobes 100A-100F are operable to cool tissues to cryoablation temperatures, and are also operable to heat tissues. For example, the cryoprobe presented in FIG. 1 is operable both to heat and to cool, depending on whether cooling gas or heating gas is supplied through Joule-Thomson orifice 80 therein.

According to a preferred embodiment of the present invention, at stage "A" a plurality of cryoprobes are inserted to a first depth into the body of a patient, in such manner that operating tips of selected ones of that plurality of cryoprobes are positioned within target 146, and operating tips of others of the inserted cryoprobes are positioned near, but outside, cryoablation target 146. Thus, in the simplified schematic presented in FIG. 14, at stage A an operating tip of probe 100B is positioned within target 146, and probes 100A, 100C, and 100D are positioned near target 146, and outside it. At this stage, probe 100B is cooled, probes 100A and 100C are heated, thereby surrounding the distal portion of target 146 with a protective heated envelope during cryoablation of a portion of target 146 by probe 100B.

After one or more freezing and thawing iterations are performed in the position shown as stage A, a surgeon partially withdraws probes 100, bringing them to the position shown as stage B. At this point, probes 100B and 100C are within target 146, and probes 100A and 100D are flanking the target. In this position, probes 100B and 100C are cooled to cryoablation temperatures, while probes 100A and 100D are gently heated.

After one or more freezing and thawing iterations are performed in the position shown as stage B, a surgeon further partially withdraws probes 100, bringing them to the position shown as stage C. At this point, probes 100B, 100C and 100D are within target 146, and probes 100A and 100E are flanking the target. In this position, probes 100B, 100C, and 100D are cooled to cryoablation temperatures, while probes 100A and 100E are gently heated.

Thus, at each stage, probes within target 146 are cooled to cryoablation temperatures, while probes surrounding (or partially surrounding) target 146 are gently heated.

Probe 100C in stage A presents a somewhat special case. The operating tip of probe C is shown as being exterior to target 146, but very close to target 146. In general, given practical limitations both on the flexibility of cryoprobe placement mechanisms and inherent inaccuracies of surgical procedure, it may be difficult or impractical to place heating and cooling probes exactly in optimal positions. In a preferred embodiment of the present invention, imaging modalities may be used in real time to determine the actual localization of probes 100, and that information may be used to calculate an appropriate combination of selected temperatures for each probe, and/or a schedule of timing for heating and cooling of those probes, so as to cause a border of a cryoablation volume 120 to be formed closely to a border 145 of cryoablation target 146. Thus, in the case, say, of probe 100C in stage A of FIG. 14, probe 100C might be heated only slightly, and probe 100A might be heated more strongly, so as to cause cryoablation volume border 102B to form near probe 100C and somewhat far from probe 100A, as shown in FIG. 14. Alternatively, control of timing of cooling and heating, including possible intermittent cooling and heating, may be used in place of, or in addition to, control of the intensity of cooling of individual probes (e.g., by variable control of gas pressure in a Joule-Thomson probe) to finely tune the influence of individual probes as desired.

FIG. 14 demonstrates a strategy for applying a method of the present invention to lateral borders of a cryoablation target 146. Strategies for handling proximal and distal borders of a cryoablation target will be presented in FIGS. 15-21 below.

Figure 15:
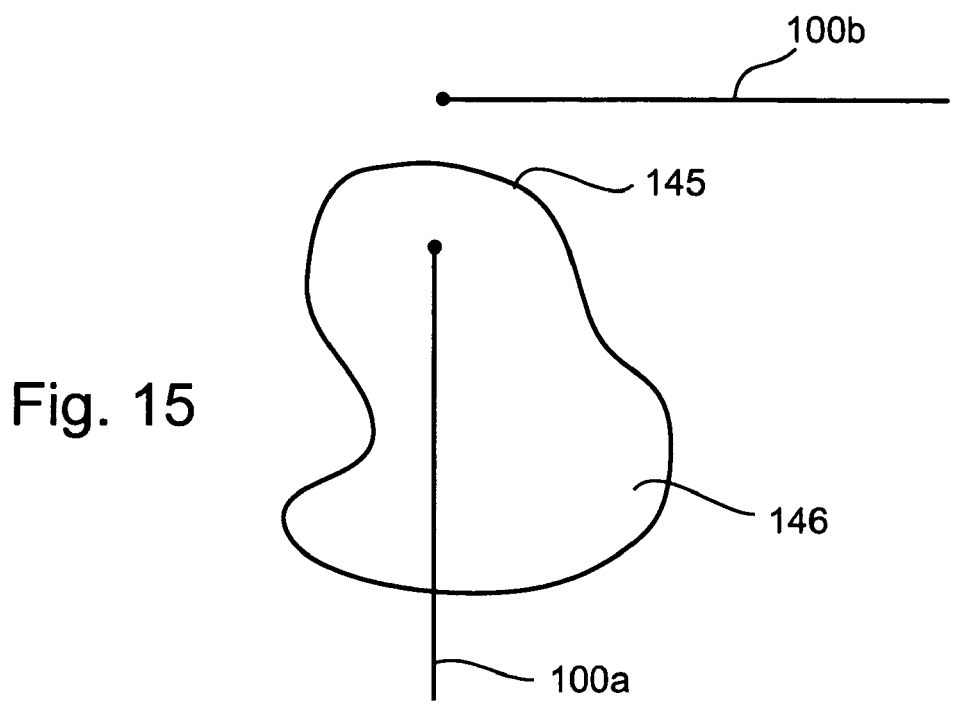
FIG. 15 is a simplified schematic of a stage in a procedure for cryoablation of a target according to an embodiment of the present invention, showing a method for treatment of a proximal or distal border of a target.

Attention is now draw to FIG. 15, which is a simplified schematic of a stage in a procedure for cryoablation of a target according to an embodiment of the present invention, showing a method for treatment of a proximal or distal border of a target.

FIG. 15 presents a cryoablation target 146, a first probe 100A penetrating a body of a patient from a first angle, and having an operating tip positioned within target 146, and a second probe 100B penetrating a body of a patient from a second angle, and having an operating tip near the operating tip of probe 100A, but positioned outside target 146. In this configuration, probe 100A may be cooled and probe 100B heated, thereby causing a border of a cryoablation volume to substantially coincide with a border 145 of target 146.

Unfortunately, a configuration such as that presented by FIG. 15 is not always practical. In the case of cryoablation of a prostate, for example, the most practicable approach to the prostate is through the perineum. Introducing all probes through the perineum, however, does not permit widely differing orientations of cryoprobes as shown in FIG. 15. Similarly, use of a guiding template 110 such as that shown in FIGS. 4 and 14 does not allow for such a configuration.

Figure 16:
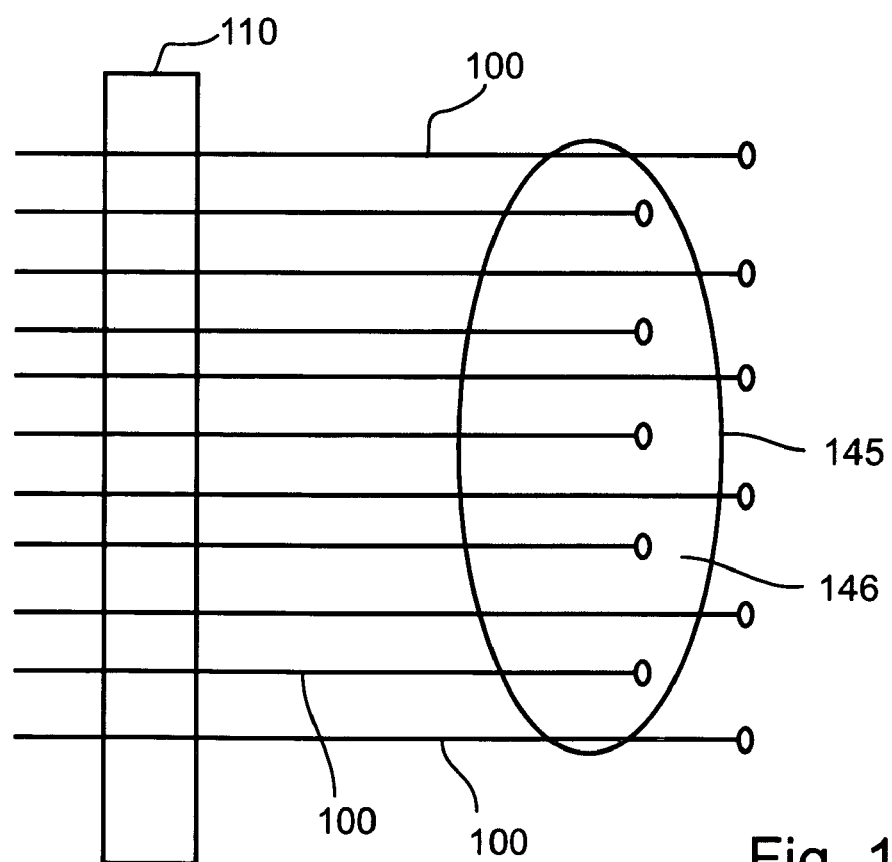
FIG. 16 is a simplified schematic of a stage in a procedure for cryoablation of a target according to an embodiment of the present invention, showing an additional method for treatment of a proximal or distal border of a target.

Attention is now drawn to FIG. 16, which is a simplified schematic of a stage in a procedure for cryoablation of a target according to an embodiment of the present invention, showing an additional method for treatment of a proximal or distal border of a target.

FIG. 16 is similar to FIG. 14, in that it displays a plurality of probes 100 inserted through a guiding template 110, and into a body of a patient. In the embodiment presented in FIG. 16, a plurality of probes 100 is positioned in a configuration appropriate for ablation at a three-dimensionally shaped distal border of a cryoablation target 146. As shown in FIG. 16, a first selected set of probes 100 may be positioned within target 146, and a second selected set of probes 100 may be positioned adjacent to a border 145 of target 146, but exterior to target 146. In this configuration, the first selected set of probes may be cooled to cryoablation temperatures while the second selected set of probes is mildly heated. Preferably, probes are selected into sets such that probes of the first set alternate with probes of the second set, as shown in FIG. 16.

The method shown in FIG. 16 may be implemented utilizing the apparatus presented in FIGS. 4-6, which is operable to introduce into a body of a patient a plurality of probes oriented in parallel orientations. The method is thus appropriate, for example, for ablating a prostate through the perineum.

With respect to fine adjustment of the position of border 102 of ablation volume 120 under the method presented in FIG. 16, we note that two options are available. Template 110, comprising an array of discrete apertures, does not offer total freedom of position in what we might call the "x" and "y" directions, across the face of template 110, yet does not restrict movement in the "z" direction, the direction of penetration into a body of a patient. A probe inserted through an aperture in template 110 may be inserted to any desired depth. Thus, the configuration provided in FIG. 16 could alternatively have been described in such a way that distances of all operating tips from the distal portion of border 145 might have been made equal across all probes 100. Instead, FIG. 16 was drawn having a certain variability in distances of various operating tips from the desired target border, with the understanding that temperature and timing of heating and cooling may be modified to compensate for minor differences of position.

We do note, however, one limitation which must be taken into account: whereas a great variability of cooling temperatures are available, and may be monitored by thermal sensors within and without probes 100, heating temperatures have an upper limit: excessive heating of tissues, while preventing unwanted damage from cold, risks causing equivalent or worse damage due to heat. In U.S. Pat. No. 6,505,629 to Mikus et. al., discussed in the background section hereinabove, it was mentioned that Mikus teaches Joule-Thomson heating wherein compressed helium of limited pressure is used, to avoid excessive heating of tissues. This method of heating, using low-pressure rather than high-pressure helium, has a disadvantage previously discussed, that use of low pressure gas, particularly in a highly miniaturized system, will result in limited heating capacity, due to the limited gas throughput that can be expected from such a system. A first alternative method would be to use Joule-Thomson heating with a heating gas, but without utilizing a heat exchanger to pre-heat that gas. This would have the advantage of allowing use of high-pressure helium, and consequently allowing increased gas throughput while avoiding high temperatures that would be obtained if pre-heating were used. This method, however, has the disadvantage of requiring separate chambers for heating (without a heat exchanger for pre-heating) and for cooling (with a heat exchanger for pre-cooling).

A preferred solution, according to a preferred embodiment of the present invention, is to heat a probe by expansion through a Joule-Thomson orifice of a mixture of gases, a mixture including both cooling gas and heating gas in a selected proportion so as to achieve a required degree of heating (or of cooling). Use of a mixture of heating gas and cooling gas enables fine control of heating and cooling, yet does not require lowered gas pressure and consequent limited throughput of gas. A system including a gas supply for this purpose is presented in FIG. 19 hereinbelow.

The method for treatment of a proximal or distal border of a cryoablation target presented by FIG. 16 has the advantage of being susceptible to implementation using standard coolable and heatable cryoprobes such as the prior art cryoprobe presented in FIG. 1. A disadvantage of the method presented by FIG. 16 is that alternating probes used for heating with probes used for cooling produces what one might call a "low resolution" effect both in heating and in cooling, thereby posing an upper limit to the accuracy of the method. FIGS. 17-21 present yet another method for treating distal and proximal borders of a cryoablation target, which method provides a "high resolution" result in comparison to the method of FIG. 16.

Figure 17:
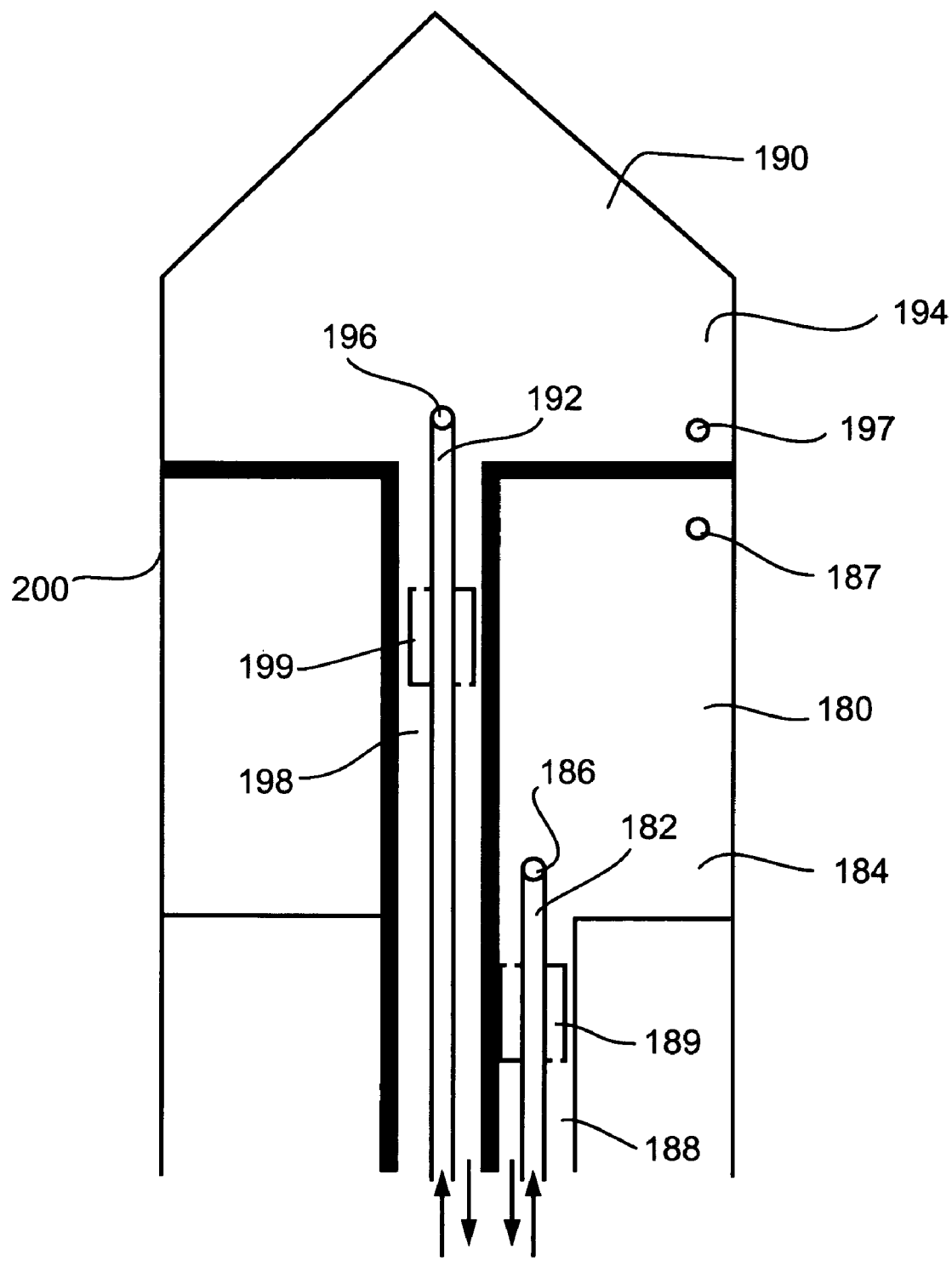
FIG. 17 is a simplified schematic of the operating section of a cryoprobe having a plurality of independently controllable treatment modules, according to an embodiment of the present invention.

Attention is now drawn to FIG. 17, which is a simplified schematic of the operating portion of a cryoprobe, comprising a plurality of independently controllable operating modules each operable to cool and to heat.

FIG. 17 presents a multi-module cryoprobe 200 having a first operating module 180 and a second operating module 190. Operating modules 180 and 190 are also sometimes referred to as "treatment modules" in the following.

Operating module 180 comprises a gas input conduit 182, a chamber 184, a Joule-Thomson orifice 186, a gas exhaust conduit 188, and a heat-exchanging configuration 189. When pressurized cooling gas is supplied through gas input conduit 182, that pressurized cooling gas expands through Joule-Thomson orifice 186 into chamber 184, cooling chamber 184. Expanded cooling gas is then exhausted through gas exhaust conduit 188, which preferably contains a heat-exchanging configuration 189 for pre-cooling incoming cooling gas in gas input conduit 182. When pressurized heating gas is supplied through gas input conduit 182, that pressurized heating gas expands through Joule-Thomson orifice 186 into chamber 184, heating chamber 184. Expanded heating gas is then exhausted through gas exhaust conduit 188, which preferably contains a heat-exchanging configuration 189 for pre-heating incoming heating gas in gas input conduit 182.

Operating module 190 is similar in function, and can be similar in construction, to operating module 180.

Operating module 190 comprises a gas input conduit 192, a chamber 194, a Joule-Thomson orifice 196, a gas exhaust conduit 198, and a heat-exchanging configuration 199. When pressurized cooling gas is supplied through gas input conduit 192, that pressurized cooling gas expands through Joule-Thomson orifice 196 into chamber 194, cooling chamber 194. Expanded cooling gas is then exhausted through gas exhaust conduit 198, which preferably contains a heat-exchanging configuration 199 for pre-cooling incoming cooling gas in gas input conduit 192. When pressurized heating gas is supplied through gas input conduit 192, that pressurized heating gas expands through Joule-Thomson orifice 196 into chamber 194, heating chamber 194. Expanded heating gas is then exhausted through gas exhaust conduit 198, which preferably contains a heat-exchanging configuration 199 for pre-heating incoming heating gas in gas input conduit 192.

Multimodule probe 200 is shown in FIG. 17 as having two treatment modules, yet alternatively probe 200 may comprise three or more treatment modules.

Each treatment module of probe 200 is designed and constructed to be independently controlled in heating and cooling. Control is preferably effected by controlling a supply of gas delivered to each module, as will be shown in FIG. 19 hereinbelow. Thus, module 180 and module 190, and additional modules if present, may be operated to cool, or to heat, at selected times and in selected degrees, each independently of the others. Thermal sensors 187 and 197 preferably provide real-time feedback to an external control system, which feedback is useful in using probe 200 to best effect. Thus, module 180 and module 190 may be operated both to cool, or both to heat, or one to heat and another to cool, in any order, at the same time or at different times. Multi-module probe 200 preferably comprises thermal insulation serving to thermally isolate modules 180 and 190 (and other modules optionally present) each from the others, to further enhance independence of operation of each module.

Figure 18C:
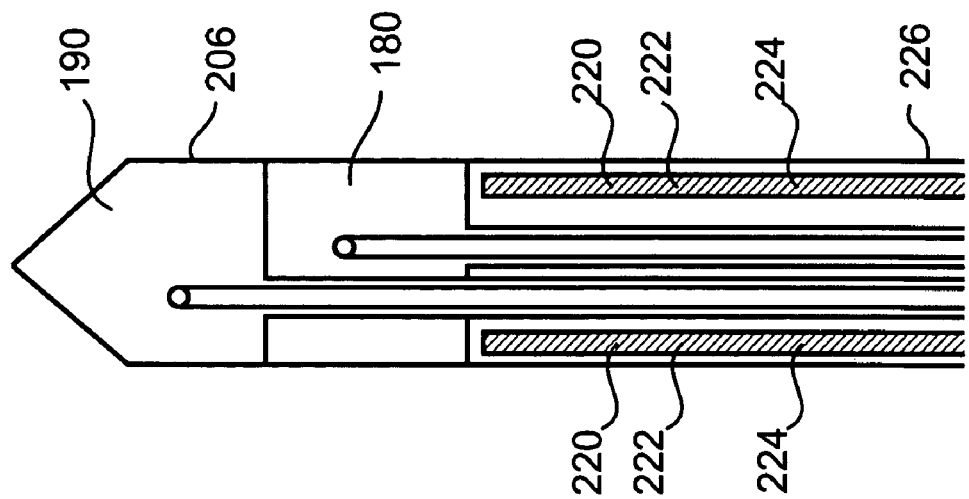
FIGS. 18A, 18B, and 18C are simplified schematics of alternate configurations of multi-module cryoprobes, according to embodiments of the present invention.
Figure 18B:
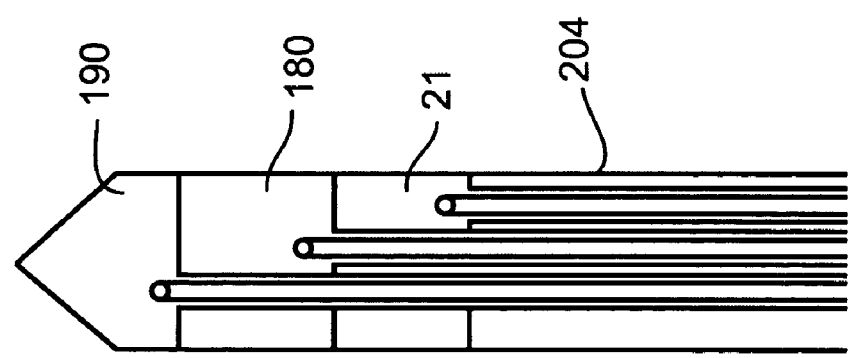
Figure 18A:
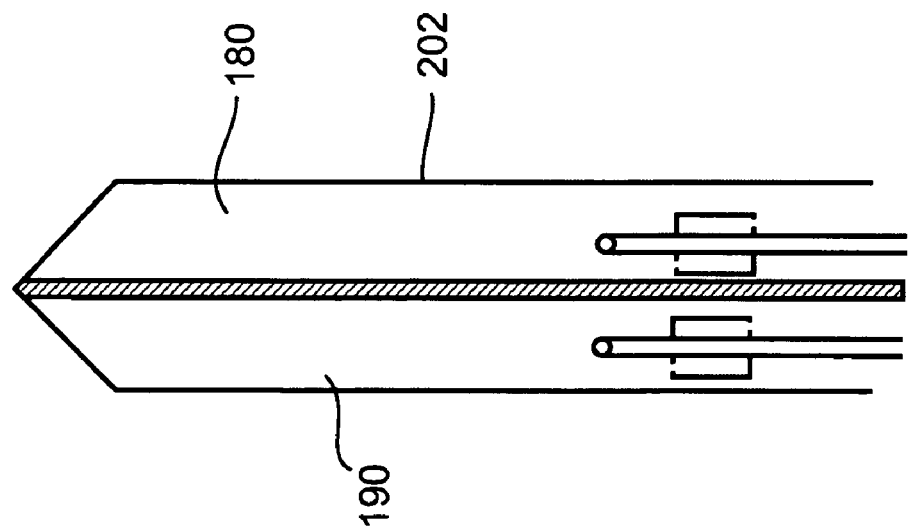

Attention is now drawn to FIGS. 18A, 18B, and 18C, which are simplified schematics of alternate configurations of multi-module cryoprobes, according to embodiments of the present invention. FIG. 18A presents a multi-module cryoprobe 202 in which modules 180 and 190 are laterally disposed (i.e., side-by-side), in contrast to multi-module cryoprobe 200 of FIG. 17, in which modules 180 and 190 are longitudinally disposed (i.e., one distal, one proximal).

FIG. 18B presents a multi-module cryoprobe 204 comprising more than two independently controllable treatment modules.

FIG. 18C presents a multi-module cryoprobe 206 comprising independently controllable treatment modules 180 and 190, and further comprising shaft isolation element 220, designed and constructed to protect tissues in a vicinity of a proximal portion of probe 206 from being damaged by cold induced by contact with shaft portion 226 of probe 206, which shaft portion is liable to be inadvertently cooled by passage therethrough of cold exhaust gasses exhausting from module 180, or from module 190, or from both. In a preferred construction, shaft isolation element 220 is thermal isolation material 222. In an alternate preferred construction, shaft isolation element 220 is an electrical resistance heater 224.

Figure 19:
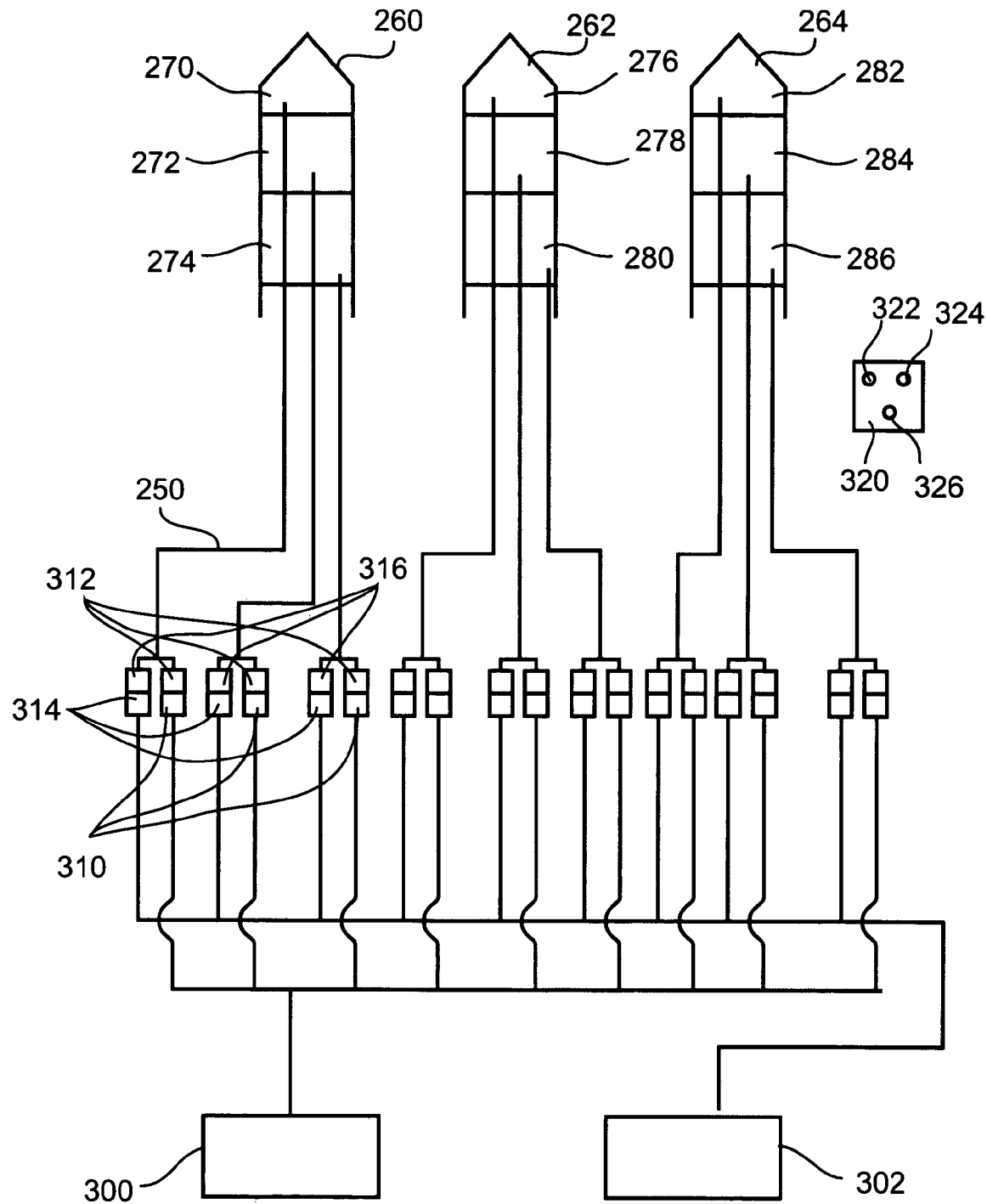
FIG. 19 is a simplified schematic of a system for cryoablation comprising a plurality of cryoprobes each having a plurality of independently controllable treatment modules, the system being operable to supply an independently selected mixture of gasses to each module of each probe, at selected times.

Attention is now drawn to FIG. 19, which is a simplified schematic of a system for cryoablation. System 250 comprises a plurality of cryoprobes, represented in the figure by cryoprobes 260, 262 and 264, each having a plurality of independently controllable operating modules, represented in the figure by modules 270, 272, 274, 276, 278, and 280, 282, 284, and 288. It is to be understood that these chosen representatives are arbitrarily chosen; cryoprobes of system 250 may be of any of the configurations presented in FIGS. 1, 17, or 18, or other configurations.

System 250 is operable to supply an independently selected mixture of gasses to each treatment module of each probe, at selected times.

System 250 comprises a source of heating gas 300 and a source of cooling gas 302. System 250 is operable to supply heating gas from heating gas source 300, through heating gas control valves 310 and one-way valves 312, to gas input conduits of a plurality of treatment modules in probes 260, 262, 264, and optionally other probes. System 250 is further operable to supply heating gas from cooling gas source 302, through cooling gas control valves 314 and one-way valves 316, to gas input conduits of a plurality of treatment modules in probes 260, 262, 264, and optionally other probes.

Valves 310 and 314 may be manual valves, but preferably they are remotely controlled valves under control of a control module 320.

Control module 320 is preferably designed and constructed to respond to data from sensors, such as thermal sensors 187 and 197, and preferably to additional thermal and pressure sensors operable to report temperatures in various parts of system 250 and in tissues of a patient, and to report pressures in various parts of system 250. Control module 320 preferably comprises a memory 322 and a processor 326, and is operable to respond to input data from the above-mentioned sensors, and to respond to operator commands, and to control valves 310 and 314, under control of algorithms 324 stored in memory 322.

In a preferred embodiment, system 250 is operable to supply cooling gas, heating gas, or a mixture of cooling gas to each treatment module of each cryoprobe of the system, thus enabling system 250 to effect various combinations of hot modules and cool modules, in a variety of configurations.

Figure 20:
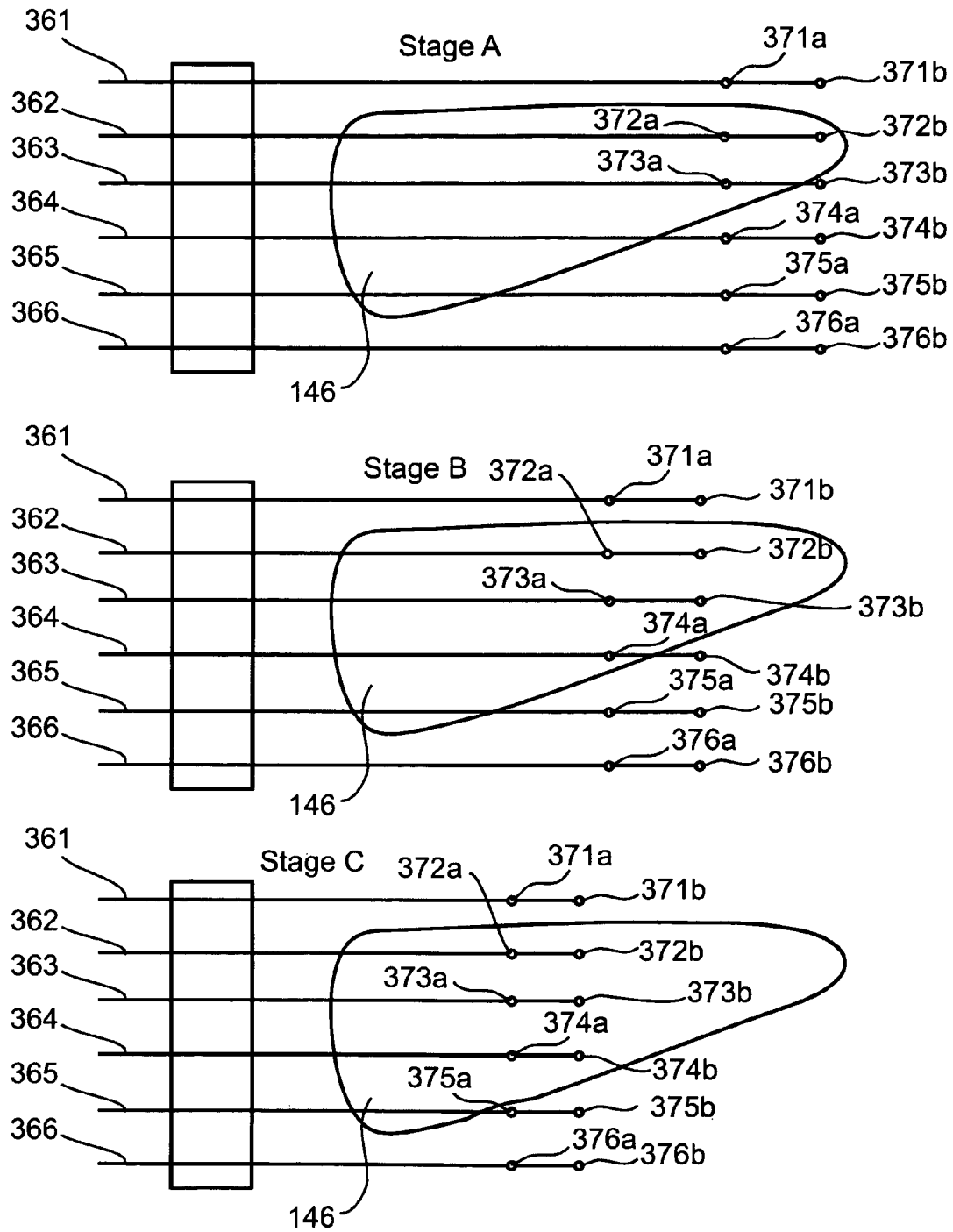
FIG. 20 is a simplified schematic showing three stages in a procedure for cryoablation of a target, according to an embodiment of the present invention, utilizing a plurality of cryoprobes each having a plurality of independently controllable operating modules.

Attention is now drawn to FIG. 20, which is a simplified schematic showing three stages in a procedure for cryoablation of a target, according to an embodiment of the present invention, utilizing a plurality of cryoprobes each having a plurality of independently controllable operating modules.

FIG. 20 is similar to FIG. 14, in that it shows three stages of "pull-back" during treatment of a cryoablation target 146. In a preferred embodiment portrayed in FIG. 20, a plurality of probes (shown as probes 361-366) are passed through a guiding template 110 and positioned in a patient's body, in and around cryoablation target 146.

Probes 361-366 are shown as each having two independently controllable treatment modules, numbered 371a, 371b, 372a, 372b, 373a, 373b, 374a, 374b, 375a, 375b, 376a, and 376b. Of course, it is to be understood that the particular configuration depicted is exemplary only, and that the invention can be practiced under a variety of alternative configurations.

In general, the treatment method comprises positioning treatment modules 371a-376b in and around cryoablation target 146, cooling those modules positioned within target 146 to cryoablation temperatures to cryoablated target 146, while heating those modules positioned external to and adjacent to target 146, thereby effecting accurately delimited cryoablation of target 146, as has been described in detail hereinabove.

Thus, in stage A, modules 372*a* and 372*b* would be cooled to cryoablation temperatures, and modules 371*a*, 371*b*, 372*b*, 373*b*, 374*a* and possible 374*b* would be activated to heat tissues in their vicinity.

In stage B, modules 372*a*, 372*b*, 373*a*, 373*b*, and 374*a* would be cooled, while modules 371*a*, 371*b*, 374*b*, 375*a*, and possibly 375*b* would be heated.

In stage C, modules 372*a*, 372*b*, 373*a*, 373*b*, 374*a*, and 374*b* would be cooled, modules 371*a*, 371*b*, 375*a*, 375*b*, and possibly 376*a* would be heated.

The effect, in each case, is to cool inside of, and to warm outside of, a selected three-dimensional shape formed to conform to a three-dimensional shape of a portion of a border of a cryoablation target, thereby causing a border of a resultant cryoablation volume to closely conform to a form of that intended cryoablation target.

Figure 21:
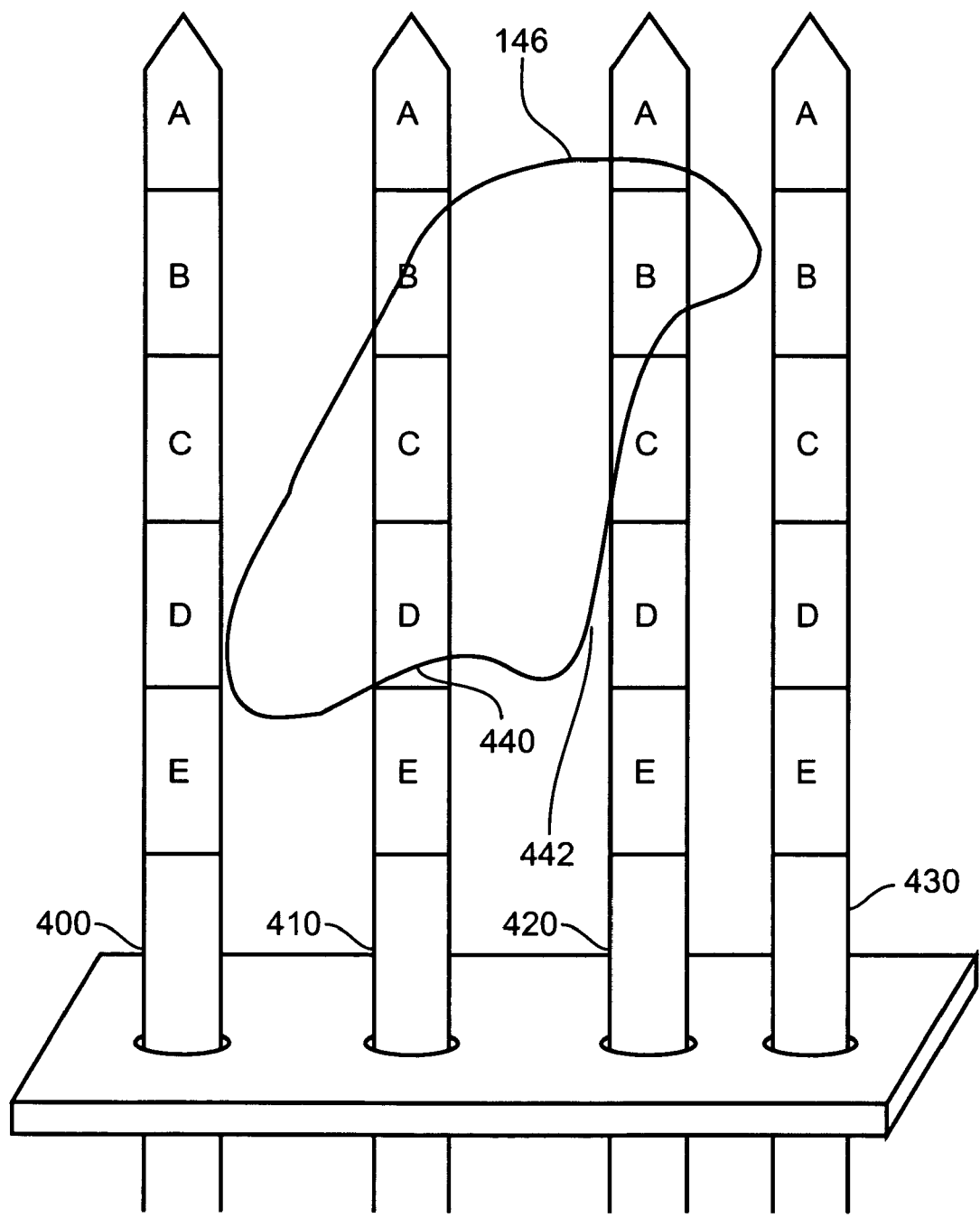
FIG. 21 is a simplified schematic of a stage in a procedure for cryoablation of a target, utilizing a plurality of cryoprobes each having a plurality of independently controllable operating modules, presenting an additional method for treatment of a proximal or distal border of a cryoablation target, according to an embodiment of the present invention.

Attention is now drawn to FIG. 21, which is a simplified schematic of a treatment of a cryoablation target by a plurality of cryoprobes each having multiple treatment modules, the treatment not requiring pullback.

In FIG. 21 a plurality of probes, represented in the figure as probes 400, 410, 420, and 430, are shown having passed through a guiding template 110 into the body of a patient, where they pass through and around a cryoablation target 146. Each probe is shown as having five treatment modules. Preferably, each module is independently controllable to heat or to cool, yet this is not a requirement of the invention. For example, it might be convenient or economical to utilize probes whose most distal and most proximal modules (modules 400A, 410A, 420A, 430A, 400E, 410E, 420E, and 430E in our example), are designed and constructed to heat but not to cool. Such modules might then utilize a heating methodology, such as electrical resistive heating, which is less appropriate for modules B, C, and D, which might be designed and constructed to be operable both to cool and to heat, for example utilizing Joule-Thomson heating and cooling.

In the examples presented in FIG. 14 and in FIG. 20, cryoablation target 146 is large in comparison to the available cooling surfaces presented by the depicted plurality of cryoprobes. Consequently, cryoablation of target 146 is executed in stages, several of which stages are presented in FIGS. 14 and 20.

In contrast, cryoablation target 146 presented by FIG. 21 is relatively small in relation to depicted cryoprobes 400, 410, 420, and 430. Moreover, cryoprobes 400, 410, 420, and 430 each comprise multiple dual-purpose treatment modules. Consequently, cryoprobes according to a preferred embodiment presented by FIG. 21 are operable to accurately cryoablated target 146 without necessitation a multi-stage pullback ablation process. Referring to the figure, it may be observed that modules 410C, 410D, and 420B are wholly or substantially positioned within target 146, and would, according to the present embodiment, be cooled to cryoablation temperatures to ablate target 146. Modules 400C, 400D, 400E, 410A, 410E, 420A, 420C, 420D, 420E, and 430B, are each external to, but near, target 146, and would, according to this embodiment, be heated during the cryoablation process, thereby producing the various positive effects generally described hereinabove.

Module 410B presents a special case, partly within and partly outside target 146. In one alternative method, module 410 may be left inactive, neither heated nor cooled. In a second alternative, calculation means such as that provided by command module 320 may be used to calculate an optimal temperature for module 410, such as to guarantee full ablation of target 146 while also minimizing ablation of tissues outside target 146. In general, the contemplated method preferably comprises calculating optimal temperatures for each module, and/or scheduling of changes in temperatures of each module over time, in order to guarantee full ablation of target 146, while also minimizing ablation of, and damage to, tissues outside target 146. Thus it may be noted, for example, that module 420D would preferably be heated to a lesser degree, or for a shorter time, than module 410E. A portion 440 of a border of target 146 falls close to the interface between module 410D and module 410E, and that border traverses probe 410 within a vicinity of module 410D. Consequently, module 410D can be used to strongly cool surrounding tissues, and module 410E may be used to heat surrounding tissues, thereby successfully producing a step-wise drop in temperature corresponding well to the shape of target 146. In contrast, a portion 442 of a border of target 146 falls near module 420D, and is relatively distant from module 410D which must provide sufficient cooling to ablate all tissues within that border. Even though module 420D is exterior to target 146, strong heating of module 420D would prevent ablation of tissues close to portion 442 and within target 146. Thus, in a preferred embodiment of the present invention, computing means such as provided by control module 320 would preferably be used to calculate optimal temperatures, over time, for each treatment module, based on whatever is known about positions of target 146 and modules 400A-430E, and further based on real-time information gleaned from thermal sensors within probes 400, 410, 420 and 430, from thermal sensors in and around tissues of target 146, and, optionally, from real-time information received from an operator or gleaned from computerize interpretation of real-time images, concerning actual positions of probes, target, and iceballs created by the cryoablation process.

Attention is now drawn to FIGS. 22-27, which present simplified schematics of additional cryoprobe configurations also useful for tailoring a cryoablation volume to a cryoablation target. Cryoprobe designs presented hereinabove are primarily designed to enable independently controlled heating and cooling of a plurality of treatment modules within a same probe. As discussed above, heating a selected module or modules while cooling other selected module or modules within a same probe facilitates accurate delimitation of an ablation volume, when a probe comprising such independently controllable treatment modules is appropriately positioned with respect to a cryoablation target, and then component treatment modules are appropriately selected and operated in heating and cooling.

FIGS. 22-27 present alternative devices also useful to produce accurately delimited ablation. These figures present cryoprobes wherein a treatment module and a thermal insulation element are positioned 'side by side' along a length of the probe. In these probes treatment module and thermal insulating element are co-positioned (laterally, i.e. one beside the other) along a length of a probe, so that cooling of the treatment module results in cooling of tissue in a first direction extending laterally (i.e. approximately radially) from a first side of the probe, but does not result in cooling (or results in reduced cooling) in a second direction extending laterally (i.e. approximately radially) from a second side of the probe. Such a cooling pattern is referred to as "laterally asymmetric cooling" in the following.

Attention is now drawn to FIG. 22, which is a simplified schematic of a cryoprobe designed to produce laterally asymmetric cooling of tissues, according to an embodiment of the present invention.

Figure 22A:
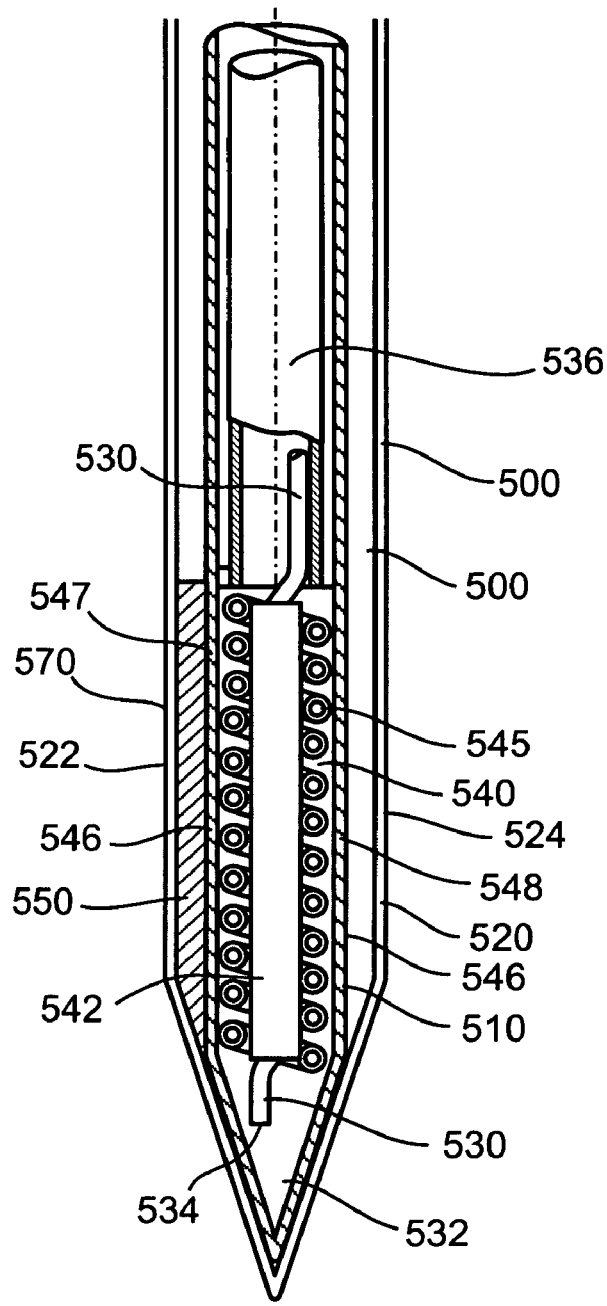
FIGS. 22A and 22B are respectively longitudinal and cross-sectional simplified schematics of a cryoprobe designed to produce laterally asymmetric cooling of tissues, according to an embodiment of the present invention.
Figure 22B:
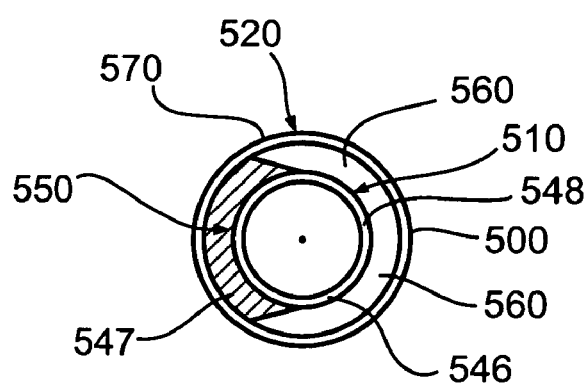

FIG. 22 presents a cryoprobe 500 designed and constructed to function, in many respects, as described hereinabove in discussion of cryoprobe 50 of FIG. 1. Cryoprobe 500 is presented in longitudinal section in FIG. 22A and in cross-section in FIG. 22B.

Cryoprobe 500 has an inner cooling unit 510 coaxially positioned within an outer sheath 520, such that sheath 520 comprises an external wall of cryoprobe 500. Inner cooling unit 510 and outer sheath 520 are here presented as being cylindrical (that is, as being of circular cross-section). Cylindrical construction of inner cooling unit 510 and outer sheath 520 is a presently preferred configuration for these elements, yet the present invention is not limited to cylindrical configurations of these elements.

Inner cooling unit 510 is a unit operable to cool to cryoablation temperatures, and is preferably (but not necessarily) also operable to heat. Inner cooling unit is here presented as a Joule-Thomson cooler or cooler/heater, yet the present invention is not limited to this configuration. In the exemplary configuration presented in FIG. 22 and in the following figures, inner cooling module 510 comprises a gas input conduit 530, an expansion chamber 532, a Joule-Thomson orifice 534, a gas exhaust conduit 536, a heat-exchanging configuration 540, and an outer wall 546. In heat-exchanging configuration 540 a portion 545 of gas input conduit 530 is spirally wrapped around a central core 542, such that during cooling operation of probe 500, spirally wrapped portion 545 of gas input conduit 530 is exposed to contact with cold expanded gasses exhausting from expansion chamber 532 and flowing towards gas exhaust conduit 536, thereby pre-cooling gasses within gas input conduit 530 as those gasses traverse gas input conduit 530 towards Joule-Thomson orifice 534, and simultaneously cooling outer wall portions 546 of inner cooling module 510. Thus, inner cooling unit 510 is designed and constructed to function as a cryoprobe of classical configuration. In the exemplary configuration presented in FIG. 22, inner cooling unit 510 resembles, and functions similarly to, a classical Joule-Thomson cryoprobe.

Cryoprobe 500 is characterized in that inner cooling module 510 is co-axially positioned within an outer sheath 520, and inner cooling module 510 and outer sheath 520 are connected, along a first portion 547 of outer wall 546, by a thermal conduction element 550, whereas a second portion 548 of outer wall 546 of inner cooling module 510 is thermally isolated from external sheath 520 by a thermal insulating element 560. Thermal conduction element 550 is made of any material which is a good conductor of heat, such as a metal. Thermal insulating element 560 shown in FIG. 22 is air, but alternative thermally insulating materials 560 might be used.

In a preferred embodiment of the present invention, thermal conduction element 550 and thermal insulation element 560 are positioned each along a portion of the circumference of cryoprobe 500 and extending 'side by side' along a length of cryoprobe 500. To avoid ambiguity, it is here noted that elements so positioned, i.e. on different sides of a common length of cryoprobe 500 (or other cryoprobe presented hereinbelow), are referred to in the claims section hereinbelow as being positioned at first and second "lateral portions" of walls (or other elements) of those cryoprobes.

It is to be noted that with respect to FIG. 22 and the following figures that thermal conduction element 550 is shown as having a distal end positioned approximately alongside a distal end of heat-exchanging configuration 540, and a proximal end positioned approximately alongside a proximal end of heat-exchanging configuration 540. Although the configuration presented in FIG. 22 is a presently preferred configuration, it is noted that thermal conduction element 550, in cryoprobe 500 and in cryoprobes presented in the following figures, may extent further proximally and/or distally than is shown in the figures. In particular, both thermal conduction element 550 and thermal insulating element 560 may be extended to appropriate portions of expansion chamber 532.

Inner cooling element 510, outer sheath 520, heat conducting element 550 and thermal isolation element 560 together constitute a laterally asymmetric tissue cooling module 570. When inner cooling module 510 is operated in cooling, asymmetric tissue cooling module 570 cools tissues adjacent to cooling portion 522 of outer sheath 520 which is adjacent to thermal conduction element 550, but does not substantially cool tissues adjacent to insulated portion 524 of outer sheath 520 which are adjacent to thermal isolation element 560. Thus, if cryoprobe 500 is inserted in a patient and positioned at a border of a cryoablation target and oriented so that cooling portion 522 is towards that cryoablation target and insulated portion 524 is facing away from that cryoablation target, and inner cooling module 510 is operated in cooling, then cryoprobe 500 will cool and cryoablate (or contribute, together with other cryoprobes, to the cryoablation of) that cryoablation target, while to protecting or partially protecting healthy tissues adjacent to probe 500 from damage due to cold induced by operation of probe 500.

FIG. 22 presents cryoprobe 500 having a single asymmetric tissue cooling module 570, yet it is to be understood that a cryoprobe comprising a plurality of asymmetric tissue cooling modules 570 may be constructed. Similarly, asymmetric tissue cooling module 570 is presented in FIG. 22 as having a smaller cooling portion 522 (constituting approximately ¼ of the circumference of module 570 in exemplary FIG. 22) and a larger insulating portion 524 (constituting approximately /3;4 of the circumference of module 570 in exemplary FIG. 22). It is to be understood that these proportions are provided by way of example only, and that other sizes and proportions may similarly be constructed. In general it is expected that a surgeon might wish to be provided with a collection of cryoprobes 500 of having asymmetric tissue cooling modules 570 of a variety of lengths and cross-sections, from which he might select one or more specific cryoprobes 500 whose particular internal configuration best fits his requirements, his selection being based on the particular size, position, and configuration of a cryoablation target he wishes to cryoablate, and the position at which he wishes to insert a cryoprobe to effect accurately delimited cryoablation.

Figure 23:
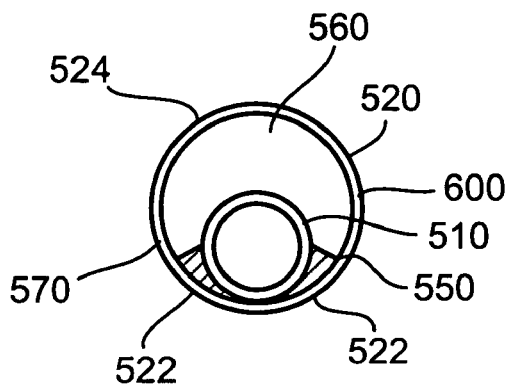
FIG. 23 is a simplified schematic of a cross-section of an alternative configuration of a cryoprobe having an asymmetric tissue cooling module, according to an embodiment of the present invention.

Attention is now drawn to FIG. 23, which is a simplified schematic of a cross-section of an alternative configuration of a cryoprobe having an asymmetric tissue cooling module 570, according to an embodiment of the present invention.

Cryoprobe 600 presented in FIG. 23 may be thought of as identical to cryoprobe 500 presented in FIG. 21, with only those differences which appear in FIG. 23. Cryoprobe 600 is characterized in that inner cooling module 510 is asymmetrically positioned within sheath 520, and is preferably positioned to be touching sheath 520. In FIG. 23 inner cooling module 510 and sheath 520 are shown as being each of circular cross-section, so that cooling module 510 touches sheath 520 at only one point of its circumference, thermal conduction material 550 being used (as in cryoprobe 500) to extend and define limits for cooling portion 522 thereof. Alternatively, either inner module 510 or external sheath 520 or both may be constructed in non-circular format in a manner which allows inner module 510 and external sheath 520 to touch, or to share a common wall, over an extended length of their circumferences. Cryoprobe 600 will of course function in a manner similar to that described above with reference to cryoprobe 500, cooling in a first direction and not cooling (or cooling substantially less) in a second direction. As with cryoprobe 500, cryoprobe 600 can be manufactured in a variety of configurations as concerning length of cooling section and portion of circumference having good thermal contact with inner cooling module 510.

Figure 24:
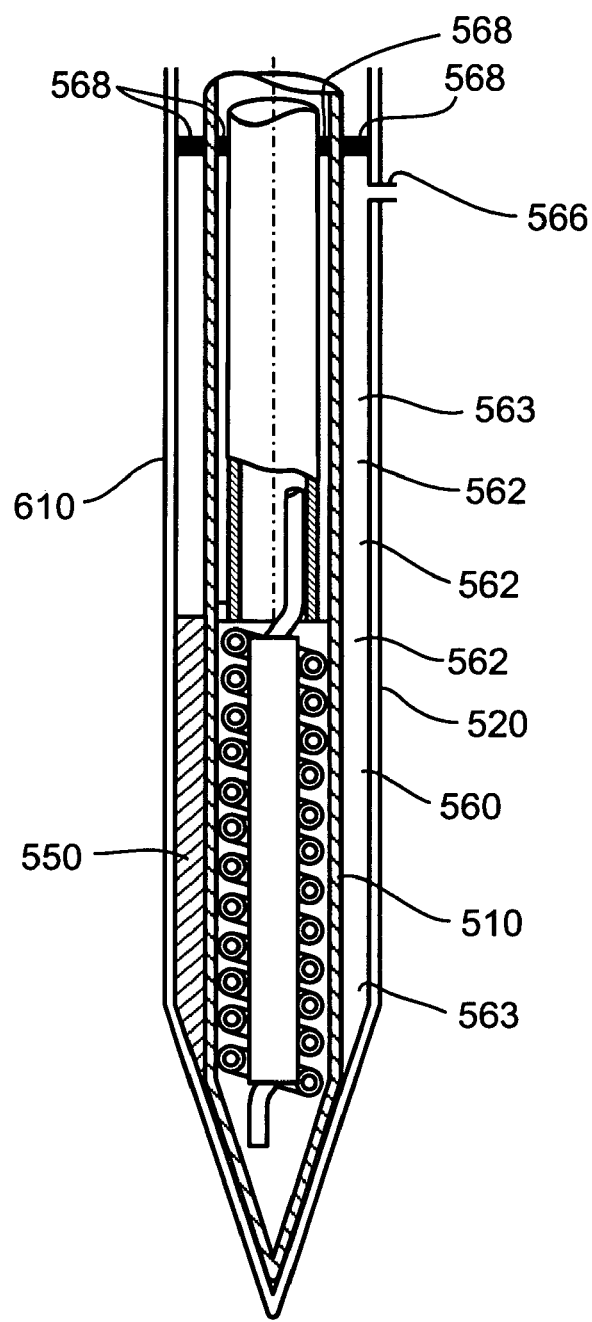
FIG. 24 a simplified schematic of an alternative configuration for a cryoprobe having an asymmetric tissue cooling module and utilizing a vacuum or partial vacuum as thermal insulation, according to an embodiment of the present invention.

Attention is now drawn to FIG. 24, which is a simplified schematic of an alternative configuration for a cryoprobe 610 having an asymmetric tissue cooling module 570 and utilizing a vacuum or partial vacuum as thermal insulation, according to an embodiment of the present invention. Cryoprobe 610 may be thought of as similar to cryoprobe 500 or to cryoprobe 600, with an additional specification concerning thermal isolating element 560. Thermal isolating element 560 of cryoprobe 610 is a vacuum (or partial vacuum) 562. Vacuum 562 is created within a volume 563 defined within sheath 520, limited by seals 568 and exterior to inner cooling module 510 and to thermal conduction material 550. Vacuum 562 is created by suction from a vacuum pump (not shown) connected to cryoprobe 610 at vacuum connector 566.

Figure 25:
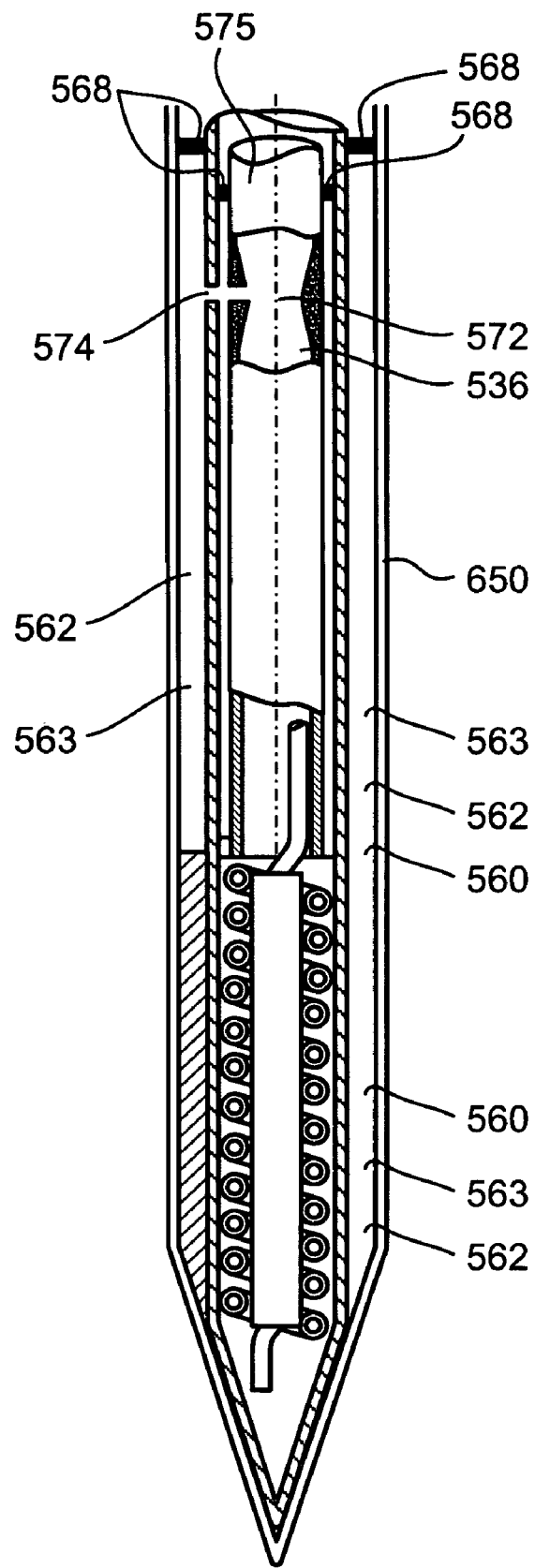
FIG. 25 is a simplified schematic of a further alternative configuration for a cryoprobe having an asymmetric tissue cooling module 570 and utilizing a vacuum or partial vacuum as thermal insulation, according to an embodiment of the present invention.

Attention is now drawn to FIG. 25, which is a simplified schematic of a further alternative configuration for a cryoprobe having an asymmetric tissue cooling module 570 and utilizing a vacuum as thermal insulation, according to an embodiment of the present invention. FIG. 25 presents a cryoprobe 650 which is similar to cryoprobe 610, but wherein vacuum 562 is created within volume 563 by a Venturi constriction 572. Venturi constriction 572 is a constriction of gas exhaust conduit 536. Pressure equalization passages 574 and 575 provide fluid communication between constriction 572 and volume 563. Gas exhausting through gas exhaust conduit 536 accelerates as it passes through constriction 572, resulting in low pressure at passage 575, thereby creating vacuum or partial vacuum 562 in volume 563, which vacuum provides thermal isolation. Thus, vacuum 562 functions as thermal isolation element 560 described hereinabove.

Figure 26:
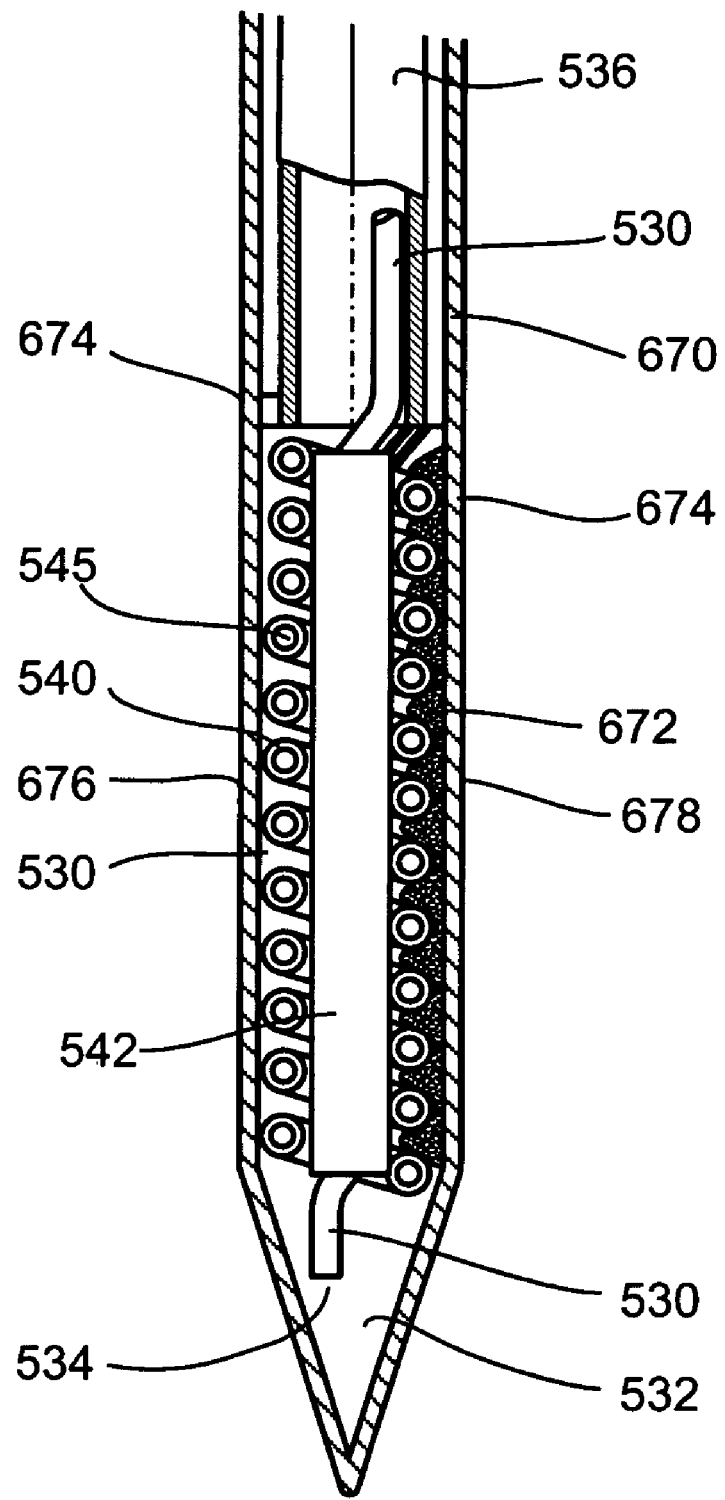
FIG. 26 is a simplified schematic of a further alternative configuration of a cryoprobe providing laterally asymmetric cooling of adjacent tissues, using thermal insulation along a side of a heat-exchanging configuration, according to an embodiment of the present invention.

Attention is now drawn to FIG. 26, which is a simplified schematic of a further alternative configuration of a cryoprobe providing laterally asymmetric cooling of adjacent tissues, according to an embodiment of the present invention. Cryoprobe 670 presented in FIG. 26 is in most respects a Joule-Thomson cryoprobe of classic design and construction, having a gas input conduit 530, an expansion chamber 532, a Joule-Thomson orifice 534, a gas exhaust conduit 536 and a heat-exchanging configuration 540 wherein a portion 545 of gas input conduit 530 is spirally wrapped around a central core 542, such that during cooling operation of probe 670, spirally wrapped portion 545 of gas input conduit 530 is exposed to contact with cold expanded gasses exhausting from expansion chamber 532, thereby pre-cooling gasses within gas input conduit 530 as those gasses traverse gas input conduit 530 towards Joule-Thomson orifice 534, and simultaneously cooling portions of outer wall 674 of cryoprobe 670. Cryoprobe 670 is characterized in that an insulating barrier 672 is provided to insulate selected portions of walls 674 of probe 670, such that first portions 676 of walls 674 cool adjacent tissues when probe 670 is operated in cooling, and second portions 678 of walls 674 are insulated by insulating barrier 672 from cooling effects of cold gasses passing through heat-exchanging configuration 540, and consequently do not strongly cool tissues adjacent to second portions 678 of walls 674. Division of walls 674 into portions 676 and portions 678 may made in any selected proportion and configuration, yet a preferred configuration is shown in FIG. 26, wherein portions 676 and 678 are laterally arranged, that is, a portion 676 runs alongside a portion 678 along a length of probe 670, enabling probe 670 to cool and cryoablate tissues located in a first directions from probe 670, while not strongly cooling and cryoablating tissues located in a second directions from probe 670.

Figure 27:
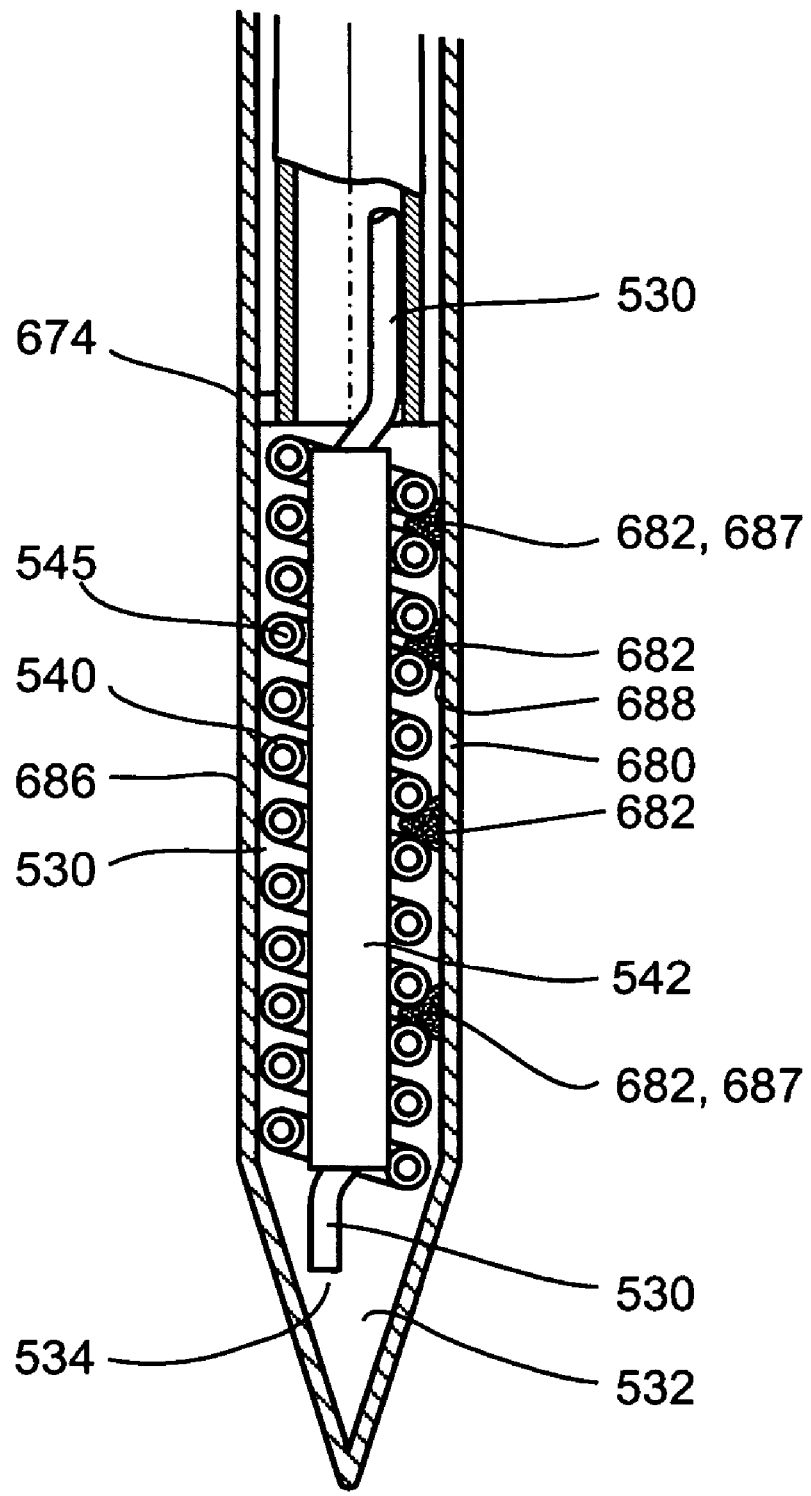
FIG. 27 is a simplified schematic of a further alternative configuration of a cryoprobe providing laterally asymmetric cooling of tissues utilizing a gas-flow blocking construction, according to an embodiment of the present invention.

Attention is now drawn to FIG. 27, which is a simplified schematic of a further alternative configuration of a cryoprobe providing laterally asymmetric cooling of tissues, according to an embodiment of the present invention.

FIG. 27 presents a cryoprobe 680, which is similar to cryoprobe 670 in its cooling features, general functionality and potential uses. Cryoprobe 680 is characterized in that fluid movement blocks 682 are provided to prevent flow of cold exhaust gasses, cooled by expansion from Joule-Thomson orifice 534 into expansion chamber 532, from flowing over or near selected portions of heat-exchanging configuration 540 and over portions 688 of external walls 674 of cryoprobe 680. As described with respect to cryoprobes presented hereinabove, heat-exchanging configuration 540 comprises a portion 545 of gas input conduit 530 spirally wrapped around a central core 542, such that during cooling operation of probe 680, spirally wrapped portion 545 of gas input conduit 530 is exposed to contact with cold expanded gasses exhausting from expansion chamber 532, thereby pre-cooling gasses within gas input conduit 530 as those gasses traverse gas input conduit 530 towards Joule-Thomson orifice 534, and simultaneously cooling portions 686 of outer wall 674 of cryoprobe 680. In distinction to prior art cryoprobes, however, cryoprobe 680 is provided with fluid movement blocks 682, preferably formed as circular ring sections 687, which blocks prevent free passage of cold gas over selected portions of the spiral windings of gas input conduit 530, thereby preventing or reducing flow of cold gasses along protected portions 688 of external walls of cryoprobe 680. Wall portions 688 thus protected do not reach extremely cold temperatures, and consequently do not cryoablate tissues contiguous to them when probe 680 is activated in cooling. Unprotected portions 686 of walls 674 are in contact with the cold gasses passing through heat-exchanging configuration 540, and consequently are cooled to cryoablation temperatures as in prior art cryoprobes It is to be noted that FIGS. 22-27 present a variety of features each of which contributes to construction of a cryoprobe capable of laterally asymmetric tissue cooling, enabling such cryoprobes to be used to cryoablate tissue extending in first lateral directions from the presented probes, while protecting from cryoablation tissues extending in second lateral directions from those probes. Features presented in FIGS. 22-27 may be combined in a variety of ways to produce cryoprobes able to provide laterally asymmetric tissue cooling. Cryoprobes 600, 670, and 680 might be combined, for example, to produce a particularly efficient version of a cryoprobe able to provide laterally asymmetric tissue cooling, and various other combinations of presented features are possible and are included within the scope of the invention.

It is further noted that since heat transmission occurs within cooled body tissues as well as within a cryoprobe, and since no thermal isolation is perfect, thermal isolation between tissues on first (cooled) and second (protected) sides of a cryoprobe according to embodiments of the present invention will not necessarily be absolute. Practically speaking, it will not generally be the case that tissue on a first side of one of the cryoprobes presented in FIGS. 22-27 will be cooled to cryoablation temperatures whereas tissues on an opposite side of that probe will not be cooled at all. Nevertheless, significant differences in cooling in directions extending from such a probe may be achieved, and accuracy of delimitation of cryoablation may greatly improved by use thereof.

It is further noted that whereas exemplary cryoprobes presented in FIGS. 22-27 are Joule-Thomson cryoprobes (i.e., are designed and constructed to be cooled by Joule-Thomson cooling), the invention herein described is not limited to cryoprobes utilizing Joule-Thomson cooling. For example, a cryoprobe utilizing evaporative cooling might yet produce laterally asymmetric tissue cooling by utilizing thermal insulation along selected lateral sides of a cryoprobe cooling module, as taught in FIG. 26. A cryoprobe cooled by evaporative cooling might also utilize fluid movement blocks 682 to limit flow of liquefied gas and/or evaporation products from liquefied gas from flowing along selected wall portions of an exterior cryoprobe wall, as taught in FIG. 27.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for sharply delimiting a cryoablation volume when cryoablating a selected cryoablation target in the body of a patient, comprising
   (a) defining a three-dimensional shape as a border of a cryoablation target;
   (b) inserting into said patient a plurality of probes each comprising at least one treatment module probe which comprises at least two treatment modules independently controllable to operate simultaneously at different temperatures;
   (c) positioning said probes so that a first set of said treatment modules is adjacent to said defined shaped border and interior to said selected cryoablation target, and a second set of said treatment modules is adjacent to said defined shaped border and exterior to said selected cryoablation target;
   (d) cooling said first set of treatment modules to cryoablation temperatures, thereby cryoablating tissues within said cryoablation target and adjacent to said border; and
   (e) heating said second set of treatment modules during said cooling of said first set of treatment modules, thereby creating a sharp temperature gradient at a vicinity of said shaped border of said cryoablation target, and simultaneously operating two of the at least two treatment modules of the multi-module probe at different temperatures,
   thereby sharply delimiting said cryoablation volume.

2. The method of claim 1, further comprising positioning said at least one multi-module probe so that at least one treatment module of said multi-module probe belongs to said first set and at least one treatment module of said multi-module probe belongs to said second set.

3. The method of claim 1, further comprising heating a first of said independently controllable treatment modules of said multi-module probe while simultaneously cooling a second of said independently controllable treatment modules of said multi-module probe.

4. The method of claim 1, further comprising heating one of said independently controllable treatment modules by expansion through a Joule-Thomson orifice of a mixture of cooling gas and heating gas.

5. The method of claim 1, further comprising orienting said probes with respect to said cryoablation target by
   (f) positioning, exterior to a patient and in a position having a known spatial relationship to said cryoablation target, a template having an array of apertures each operable to orient a probe passing therethrough to a predetermined angle with respect to said template; and
   (g) passing a plurality of said probes through ones of said array of apertures, and thence into said patient,
   thereby orienting said inserted probes with respect to said cryoablation target.

6. The method of claim 1, wherein a first of said independently controllable treatment modules comprises a first gas input lumen and a first expansion chamber, and a second of said independently controllable treatment modules comprises a second gas input lumen distinct from said first gas input lumen and a second expansion chamber distinct from said first expansion chamber.

7. The method of claim 5, wherein said template is designed and constructed to ensure parallel orientations of a plurality of cryoprobes inserted therethrough.

8. The method of claim 7, wherein one of said probes comprises an external marking on said probe, designed and constructed to render visible to an operator a depth of penetration of said probe through said template.

9. The method of claim 1, wherein for each portion of said target border bordering on tissues cooled by a treatment module of said first set of treatment modules, there is provided one of said second set of treatment modules positioned outside said border portion and used to heat tissues outside said border portion while tissues inside said border portion are being cooled.

10. A method for minimizing damage to tissues surrounding a cryoablation target when cryoablating said target, comprising
   (a) defining a three-dimensional shape as a border of a cryoablation target;
   (b) inserting into a patient a plurality of probes each comprising at least one treatment module, at least one of said plurality of probes being a multi-module probe which comprises at least two independently controllable treatment modules;
   (c) positioning said probes so that a first set of said treatment modules is inside said cryoablation target, and a second set of said treatment modules is exterior to said target and surrounds at least a portion of said target, and positioning said at least one multi-module probe so that at least one module of said multi-module probe belongs to said first set and at least one module of said multi-module probe belongs to said second set;
   (d) cooling said first set of treatment modules to cryoablation temperatures, thereby ablating tissues within said target; and (e) heating said second set of treatment modules during cooling of said first set of treatment modules, thereby preventing cooling of tissues surrounding said cryoablation target, thereby minimizing damage to tissues surrounding said cryoablation target while cryoablating said target.

11. The method of claim 10, wherein said second set of treatment modules creates an envelope of heated tissues which entirely surrounds said cryoablation target.

12. The method of claim 10, further comprising positioning said first set of treatment modules with an organ, and wherein cooling of said first set of treatment modules entirely ablates said organ.

13. The method of claim 12, wherein said organ is a prostate.

14. The method of claim 10, further comprising positioning said first set of treatment modules within a tumor, and wherein cooling of said first set of treatment modules entirely ablates said tumor.

15. The method of claim 10, wherein each treatment module of said first set of treatment modules is positioned adjacent to at least one treatment module of said second set of treatment modules.

16. A method for accurately delimited cryoablation of a target, comprising
  (a) inserting into a patient a plurality of cryoprobes, each of said cryoprobes comprising at least one treatment module and at least one of said cryoprobes being a multi-module cryoprobe which comprises a plurality of treatment modules;
  (b) positioning said cryoprobes so that a first set of said treatment modules are positioned within said target and a second set of said treatment modules are positioned exterior to said target, said multi-module cryoprobe being so positioned that at least one treatment module of said multi-module probe belongs to said first set and at least one treatment module of said multi-module probe belongs to said second set; and
  (c) warming said second set of treatment modules while cooling said first set of treatment modules to cryoablation temperatures, thereby creating a warming envelope around said target while cryoablating said target, thereby effecting accurately delimited cryoablation of said target.

17. The method of claim 16, further comprising utilizing imaging modalities to visual said target and said cryoprobes.

18. The method of claim 16, wherein treatment modules of said first set of treatment modules are cooled by Joule-Thomson cooling.

19. The method of claim 16, wherein treatment modules of said second set of treatment modules are heated by Joule-Thomson heating.

20. The method of claim 19, wherein said Joule-Thomson heating is provided by expansion of a mixture of cooling gas and heating gas.

21. A method for cryoablating a target while minimizing damage to tissues surrounding said target, comprising:
  (a) introducing into said target a plurality of first treatment modules operable to perform cryogenic cooling;
  (b) introducing near said target a plurality of second treatment modules operable to heat tissues;
  (c) utilizing said first treatment modules to cool tissues of said target to cryoablation temperatures; and
  (d) utilizing said second treatment modules to heat tissues so as to provide an envelope of heated tissues which entirely surrounds said target during cryoablation of said target.

22. The method of claim 21, further comprising utilizing at least one multi-module cryoprobe which comprises at least one of said first treatment modules and at least one of said second treatment modules.

23. The method of claim 22, further comprising positioning said multi-module cryoprobe so that it completely traverses said cryoablation target, and so that at least one treatment module of said probe is positioned distal to said target, at least one treatment module of said probe is positioned within said target, and at least one treatment module of said probe is positioned proximal to said target.

24. The method of claim 21, further comprising calculating for a pluarality of said treatment modules an optional schedule of treatment temperatures, so as to ensure complete ablation of said cryoablation target while maximizing protection of tissues outside said target.

25. The method of claim 21, comprising executing said method in several stages extended over time, utilizing a pullback procedure.

* * * * *